United States Patent
Aotsuka et al.

[11] Patent Number: 6,136,831
[45] Date of Patent: Oct. 24, 2000

[54] PYRAZOLE DERIVATIVES AND COX INHIBITORS CONTAINING THEM

[75] Inventors: Tomoji Aotsuka; Nagatoshi Wagatsuma, both of Hamura; Hideo Kato, Toyohashi; Naoki Ashizawa, Hamura, all of Japan

[73] Assignee: Grelan Pharmaceutical Co., Ltd., Tokyo, Japan

[21] Appl. No.: 09/402,433

[22] PCT Filed: Apr. 10, 1998

[86] PCT No.: PCT/JP98/01664

§ 371 Date: Oct. 7, 1999

§ 102(e) Date: Oct. 7, 1999

[87] PCT Pub. No.: WO98/46594

PCT Pub. Date: Oct. 22, 1998

[30] Foreign Application Priority Data

Apr. 11, 1997 [JP] Japan ..................................... 9-108299

[51] Int. Cl.$^7$ ................... A61K 31/4184; A61K 31/423; A61K 31/428; C07D 417/04; C07D 403/04
[52] U.S. Cl. ........................ 514/367; 514/375; 514/394; 548/152; 548/178; 548/217; 548/306.1
[58] Field of Search ..................... 548/152, 178, 548/217, 306.1; 514/367, 375, 394

[56] References Cited

FOREIGN PATENT DOCUMENTS

| 0 745 596 | 12/1996 | European Pat. Off. . |
| 0 826 676 | 3/1998 | European Pat. Off. . |
| 95/18799 | 7/1995 | WIPO . |

*Primary Examiner*—Laura L. Stockton
*Attorney, Agent, or Firm*—Wenderoth, Lind & Ponack, L.L.P.

[57] ABSTRACT

The purpose is to provide anti-inflammatory agents which have potent pharmacological actions and exert a selective inhibitory activity on COX-2, thereby being expected to reduce adverse effects such as disorders in gastric mucosa. The present invention encompasses a compound of the formula (1):

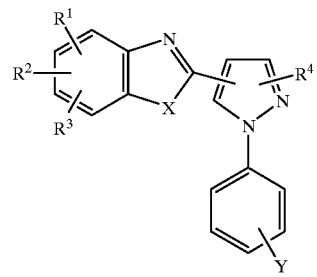

(1)

wherein $R^1$ is hydrogen or halogen, $R^2$ and $R^3$ are each independently hydrogen, halogen, lower alkyl, lower alkoxy, hydroxy or lower alkanoyloxy, $R^4$ is lower haloalkyl or lower alkyl, X is sulfur, oxygen or NH, and Y is lower alkylthio, lower alkylsulfonyl or sulfamoyl, which exerts superior anti-inflammatory activity, and highly inhibits COX-2 induced in inflamed sites, with less inhibitory action on COX-1 present in stomach, kidney, etc. Pharmaceutical agents comprising the compound of the present invention are provided as selective COX-2 inhibitors, and anti-inflammatory agents rarely accompanying adverse actions including attacks on gastric mucosa.

6 Claims, No Drawings

PYRAZOLE DERIVATIVES AND COX INHIBITORS CONTAINING THEM

The application is a 371 of PCT/JP98/01664 filed Apr. 10, 1998.

FIELD OF THE INVENTION

The present invention relates to novel pyrazole derivatives which inhibit cyclooxygenase-2 (COX-2), or pharmaceutically acceptable salts thereof, and pharmaceutical compositions comprising the same. The compounds of the present invention are useful in treating inflammation and a variety of diseases associated therewith.

BACKGROUND OF THE INVENTION

It has been known that conventional non-steroidal anti-inflammatory drugs (NSAIDs), representatives of which include aspirin, indomethacin, etc., control the biosynthesis of prostaglandins, certain chemical mediators for inflammation, via the inhibition of cyclooxygenase (COX) which is a synthase responsible for the formation of prostaglandins from arachidonic acid, thereby exerting anti-inflammatory action. However, prostaglandins are involved in a variety of physiological actions including not only inflammation but also the inhibition of gastric secretion and the increase of mucosal blood flow. Since the conventional NSAIDs also inhibit the biosynthesis of certain prostaglandins responsible for other physiological roles than inflammation, they frequently have a high potential for raising adverse side effects such as attacks on gastric mucosa and kidney. Accordingly, the clinical usefulness of the NSAIDs is often restricted.

Recently, it has been found that there are isozymes of COX. Thus, one form of COX, named "COX-1", which has been known in the art up until recently, exists systemically and constantly in stomach, kidney, etc. Another form of COX, named "COX-2", which has been discovered newly, is inducible at the site of an inflammatory stimulus. It is believed that the conventional NSAIDs inhibit both COX-1 and COX-2, with the result that such side effects appear. When selective COX-2 inhibitors are available, it is therefore expected that such selective COX-2 inhibitors would exert predominantly desirable anti-inflammatory action whereby they would reduce the aforementioned side effects entailed by the conventional NSAIDs with non-selective COX inhibiting activity.

From such an angle, up until now, some compounds have been synthesized with a view to exploring selective COX inhibitors. For anti-inflammatory pyrazole derivatives among them, those disclosed in JP, 1-52758, A (1989); JP, 3-141261, A (1991); JP, 5-246997, A (1993); etc., have been known. Further, WO, 95/15315, A1 (1995); WO, 95/15316, A1 (1995); WO, 95/15318, A1 (1995); etc., disclose pyrazole derivatives, part of which have selective COX-2 inhibitory and anti-inflammatory activity.

However, these compounds are not satisfactory medicaments for solving the above problems, so the development of anti-inflammatory drugs with significantly selective COX-2 inhibiting activity together with more advantageous pharmacological action and safety is still desired.

DISCLOSURE OF THE INVENTION

The present inventors have conducted an extensive research on various compounds in order to solve the above problems. As a result, the present inventors have succeeded in producing novel pyrazole derivatives with a nitrogen-containing heterocyclic group such as a benzothiazole moiety which exert selective inhibition against COX-2. Further, the present inventors have found that the compounds of the present invention are unexpectedly superior to the conventional NSAIDs and they are qualified as COX inhibitors from aspects of pharmacological action and safety and succeeded in accomplishing this invention.

Thus, the present invention provides a compound of the formula (1):

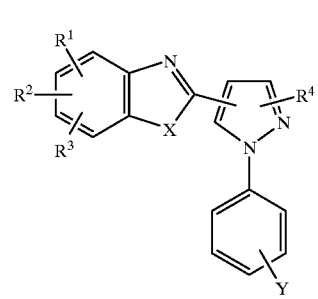

wherein $R^1$ is hydrogen or halogen, $R^2$ and $R^3$ are each independently hydrogen, halogen, lower alkyl, lower alkoxy, hydroxy or lower alkanoyloxy, $R^4$ is lower haloalkyl or lower alkyl, X is sulfur, oxygen or NH, and Y is lower alkylthio, lower alkylsulfonyl or sulfamoyl, or a pharmaceutically acceptable salt thereof; and a pharmaceutical composition comprising said compound (1) or a pharmaceutically acceptable salt thereof in admixture with a pharmaceutically acceptable carrier.

BEST MODES OF CARRYING OUT THE INVENTION

The compounds of the present invention are those which have the following unique features:

① a nitrogen-containing heterocyclic moiety (hereinafter also referred to "benzazole group") selected from the group consisting of a benzothiazole group, a benzoxazole group and a benzimidazole group, and ② a phenyl moiety substituted with a sulfur-containing radical selected from the group consisting of a lower alkylthio group, a lower alkylsulfonyl group and a sulfamoyl group, on the pyrazole ring. Described below are preferred embodiments of the present invention.

1) A compound of the formula (1):

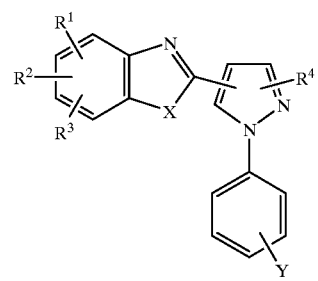

wherein $R^1$ is hydrogen or halogen, $R^2$ and $R^3$ are each independently hydrogen, halogen, lower alkyl, lower alkoxy, hydroxy or lower alkanoyloxy, $R^4$ is lower haloalkyl or lower alkyl, X is sulfur, oxygen or NH, and Y is lower alkylthio, lower alkylsulfonyl or sulfamoyl, or a pharmaceutically acceptable salt thereof;
2) a compound of the formula (2):

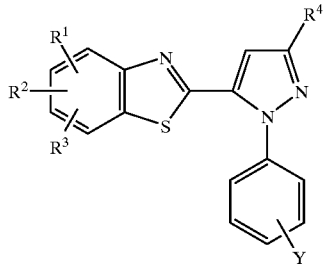

(2)

wherein $R^1$ is hydrogen or halogen, $R^2$ and $R^3$ are each independently hydrogen, halogen, lower alkyl, lower alkoxy, hydroxy or lower alkanoyloxy, $R^4$ is lower haloalkyl or lower alkyl, and Y is lower alkylthio, lower alkylsulfonyl or sulfamoyl,
or a pharmaceutically acceptable salt thereof;
3) the compound according to the above 2), wherein $R^4$ is lower haloalkyl, and Y is lower alkylsulfonyl, or sulfamoyl, or a pharmaceutically acceptable salt thereof;
4) a pharmaceutical composition which comprises an effective amount of a compound according to the above 1) or a pharmaceutically acceptable salt thereof in admixture with a pharmaceutically acceptable carrier;
5) a COX-2 inhibitor comprising a compound according to the above 1) or a pharmaceutically acceptable salt thereof; and
6) an anti-inflammatory agent comprising a compound according to the above 1) or a pharmaceutically acceptable salt thereof.

As used herein for the aforementioned compounds (1) and (2), the term "halogen" refers to fluorine, chlorine, or bromine, preferably fluorine. As used herein, the term "lower alkyl" refers to alkyl containing 1 to 3 carbon atoms, such as methyl, ethyl, propyl, and isopropyl. As used herein, the term "lower alkoxy" refers to alkoxy containing 1 to 3 carbon atoms, such as methoxy, ethoxy, propoxy, and isopropoxy. As used herein, the term "lower alkanoyloxy" refers to alkanoyloxy containing 2 to 4 carbon atoms, such as acetoxy, propionyloxy, butyryloxy, and isobutyryloxy.

As used herein, the term "lower haloalkyl" refers to lower alkyl substituted with halogen, such as fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloropropyl, bromomethyl, and bromoethyl.

As used herein, the term "lower alkylthio" refers to alkylthio containing 1 to 3 carbon atoms, such as methylthio, ethylthio, propylthio, and isopropylthio. As used herein, the term "lower alkylsulfonyl" refers to alkylsulfonyl containing 1 to 3 carbon atoms, such as methylsulfonyl, ethylsulfonyl, propylsulfonyl, and isopropylsulfonyl.

Preferably, compounds according to the present invention have the structural formula (1). Still more preferably, compounds according to the present invention have the structural formula (2). Most preferably, compounds according to the instant invention have the structural formula (2) wherein $R^4$ is lower haloalkyl and Y is lower alkylsulfonyl or sulfamoyl.

Described below are examples of the compounds according to the present invention:
2-[1-(4-methylsulfonylphenyl)-3-trifluoromethyl-1H-pyrazol-5-yl]benzothiazole
4-fluoro-2-[1-(4-methylsulfonylphenyl)-3-trifluoromethyl-1H-pyrazol-5-yl]benzothiazole
5-fluoro-2-[1-(4-methylsulfonylphenyl)-3-trifluoromethyl-1H-pyrazol-5-yl]benzothiazole
6-fluoro-2-[1-(4-methylsulfonylphenyl)-3-trifluoromethyl-1H-pyrazol-5-yl]benzothiazole
7-fluoro-2-[1-(4-methylsulfonylphenyl)-3-trifluoromethyl-1H-pyrazol-5-yl]benzothiazole
6-chloro-2-[1-(4-methylsulfonylphenyl)-3-trifluoromethyl-1H-pyrazol-5-yl]benzothiazole
6-methoxy-2-[1-(4-methylsulfonylphenyl)-3-trifluoromethyl-1H-pyrazol-5-yl]benzothiazole
4-[5-(benzothiazol-2-yl)-3-trifluoromethyl-1H-pyrazol-1-yl]-benzenesulfonamide
4-[5-(4-fluorobenzothiazol-2-yl)-3-trifluoromethyl-1H-pyrazol-1-yl]benzenesulfonamide
4-[5-(5-fluorobenzothiazol-2-yl)-3-trifluoromethyl-1H-pyrazol-1-yl]benzenesulfonamide
4-[5-(6-fluorobenzothiazol-2-yl)-3-trifluoromethyl-1H-pyrazol-1-yl]benzenesulfonamide
4-[5-(7-fluorobenzothiazol-2-yl)-3-trifluoromethyl-1H-pyrazol-1-yl]benzenesulfonamide
4-[5-(6-chlorobenzothiazol-2-yl)-3-trifluoromethyl-1H-pyrazol-1-yl]benzenesulfonamide
4-[5-(6-methoxybenzothiazol-2-yl)-3-trifluoromethyl-1H-pyrazol-1-yl]benzenesulfonamide
6-methyl-2-[1-(4-methylsulfonylphenyl)-3-trifluoromethyl-1H-pyrazol-5-yl]benzothiazole
4-[5-(6-methylbenzothiazol-2-yl)-3-trifluoromethyl-1H-pyrazol-1-yl]benzenesulfonamide
4-[5-(7-chlorobenzothiazol-2-yl)-3-trifluoromethyl-1H-pyrazol-1-yl]benzenesulfonamide
6-fluoro-5-methyl-2-[1-(4-methylsulfonylphenyl)-3-trifluoromethyl-1H-pyrazol-5-yl]benzothiazole
4-[5-(6-fluoro-5-methylbenzothiazol-2-yl)-3-trifluoromethyl-1H-pyrazol-5-yl]benzenesulfonamide
4-[5-(4-methoxybenzothiazol-2-yl)-3-trifluoromethyl-1H-pyrazol-1-yl ]benzenesulfonamide Further, representative compounds according to the present invention include the following compounds wherein each 3-trifluoromethyl of the aforementioned embodiments of the 5compounds is replaced with either 3-difluoromethyl or 3-pentafluoroethyl:
2-[1-(4-methylsulfonylphenyl)-3-difluoromethyl-1H-pyrazol-5-yl]benzothiazole
4-fluoro-2-[1-(4-methylsulfonylphenyl)-3-difluoromethyl-1H-pyrazol-5-yl]benzothiazole
5-fluoro-2-[1-(4-methylsulfonylphenyl)-3-difluoromethyl-1H-pyrazol-5-yl]benzothiazole
6-fluoro-2-[1-(4-methylsulfonylphenyl)-3-difluoromethyl-1H-pyrazol-5-yl]benzothiazole
7-fluoro-2-[1-(4-methylsulfonylphenyl)-3-difluoromethyl-1H-pyrazol-5-yl]benzothiazole
6-chloro-2-[1-(4-methylsulfonylphenyl)-3-difluoromethyl-1H-pyrazol-5-yl]benzothiazole
6-methoxy-2-[1-(4-methylsulfonylphenyl)-3-difluoromethyl-1H-pyrazol-5-yl]benzothiazole
4-[5-(benzothiazol-2-yl)-3-difluoromethyl-1H-pyrazol-1-yl]-benzenesulfonamide
4-[5-(4-fluorobenzothiazol-2-yl)-3-difluoromethyl-1H-pyrazol-1-yl]benzenesulfonamide
4-[5-(5-fluorobenzothiazol-2-yl)-3-difluoromethyl-1H-pyrazol-1-yl]benzenesulfonamide
4-[5-(6-fluorobenzothiazol-2-yl)-3-difluoromethyl-1H-pyrazol-1-yl]benzenesulfonamide
4-[5-(7-fluorobenzothiazol-2-yl)-3-difluoromethyl-1H-pyrazol-1-yl]benzenesulfonamide 4-[5-(6-chlorobenzothiazol-2-yl)-3-difluoromethyl-1H-pyrazol-1-yl]benzenesulfonamide 4-[5-(6-methoxybenzothiazol-2-yl)-3-difluoromethyl-1H-pyrazol-1-yl]benzenesulfonamide 6-methyl-2-[1-(4-methylsulfonylphenyl)-3-difluoromethyl-1H-pyrazol-5-yl]benzothiazole 4-[5-(6-methylbenzothiazol-2-yl)-3-difluoromethyl-1H-pyrazol-1-yl]benzenesulfonamide 4-[5-(7-chlorobenzothiazol-2-yl)-3-difluoromethyl-1H-pyrazol-1-yl]benzenesulfonamide 6-fluoro-5-methyl-2-[1-(4-methylsulfonylphenyl)-3-difluoromethyl-1H-pyrazol-5-yl]benzothiazole 4-[5-(6-fluoro-5-methylbenzothiazol-2-yl)-3-difluoromethyl-1H-pyrazol-5-yl]benzenesulfonamide 4-[5-(4-methoxybenzothiazol-2-yl)-3-difluoromethyl-1H-pyrazol-1-yl]benzenesulfonamide 6-methyl-2-[1-(4-methylsulfonylphenyl)-3-pentafluoroethyl-1H-pyrazol-5-yl]benzothiazole 4-[5-(6-methylbenzothiazol-2-yl)-3-pentafluoroethyl-1H-pyrazol-1-yl]benzenesulfonamide Representative compounds coming within the scope of the present invention also include the following:

4-[5-(6-fluorobenzoxazol-2-yl)-3-trifluoromethyl-1H-pyrazol-1-yl]benzenesulfonamide 4-[5-(6-methylbenzoxazol-2-yl)-3-trifluoromethyl-1H-pyrazol-1-yl]benzenesulfonamide 6-fluoro-2-[1-(4-methylsulfonylphenyl)-3-difluoromethyl-1H-pyrazol-5-yl]benzoxazole 6-methyl-2-[1-(4-methylsulfonylphenyl)-3-difluoromethyl-1H-pyrazol-5-yl]benzoxazole 4-[5-(7-fluorobenzoxazol-2-yl)-3-difluoromethyl-1H-pyrazol-1-yl]benzenesulfonamide 7-fluoro-2-[1-(4-methylsulfonylphenyl)-3-difluoromethyl-1H-pyrazol-5-yl]benzoxazole 6-fluoro-2-[1-(4-methylsulfonylphenyl)-3-trifluoromethyl-1H-pyrazol-5-yl]benzimidazole 4-[5-(6-fluorobenzimidazol-2-yl)-3-trifluoromethyl-1H-pyrazol-1-yl]benzenesulfonamide 7-fluoro-2-[1-(4-methylsulfonylphenyl)-3-difluoromethyl-1H-pyrazol-5-yl]benzimidazole 4-[5-(7-fluorobenzimidazol-2-yl)-3-difluoromethyl-1H-pyrazol-1-yl]benzenesulfonamide The present invention also encompasses pharmaceutically acceptable salts of the pyrazole derivative having the formula (1). Such salts include those formed from any of medically or pharmaceutically utilizable non-toxic or low toxic inorganic or organic acids. Examples of the salts are hydrochloride, hydrobromide, sulfate, acetate, propionate, citrate, succinate, tartarate, methanesulfonate, etc.

The compounds of the present invention can be prepared by one of various routes. For instance, the compounds of the formula (1) wherein X=sulfur can be prepared by one of the following schemes or modifications thereof:

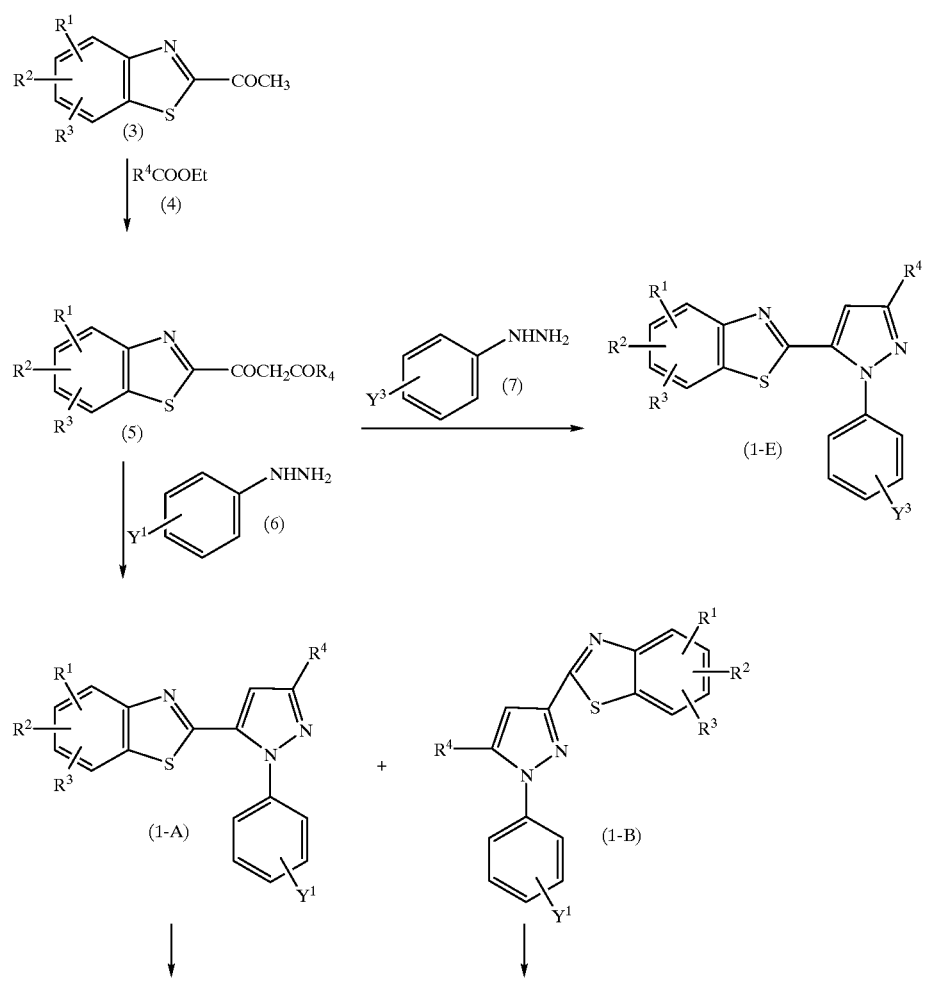

-continued

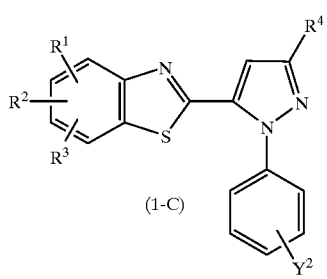

(1-C)

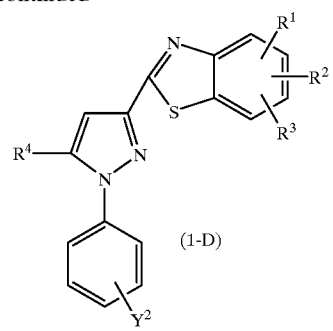

(1-D)

In the aforementioned Scheme, the compounds of the formula (5) wherein $R^1$, $R^2$, $R^3$ and $R^4$, all have the meanings given above can be prepared by reacting a compound of the formula (3) wherein $R^1$, $R^2$ and $R^3$, all have the meanings given above with a compound of the formula (4) wherein $R^4$ has the meaning given above in the presence of a base, preferably under an inert gas atmosphere, such as nitrogen. Bases used in this reaction may include alkali metal alkoxides, alkali metal hydrides, alkali metal amides, and the like. Examples of the base are sodium methoxide, sodium ethoxide, potassium t-butoxide, lithium hydride, sodium hydride, potassium hydride, sodium amide, potassium amide, lithium diisopropylamide, etc. The reaction can be conducted in the presence of or in the absence of a solvent. When the reaction is conducted in solvents, it is often convenient to use conventional solvents which are free from any adverse action on the reaction. Preferred examples of such solvents are tetrahydrofuran (THF), dimethylformamide (DMF), ether, methylene chloride, benzene, toluene, etc. The reaction temperature range is about −80 to 100° C. and preferably about −30° C. to room temperature. The compounds of the formula (3) can be prepared according to known methods (Bull. Chem. Soc. Jpn.), 61, 3637 (1988); J. Chem. Soc., (C), 1971, 1747, the disclosure of which is herein incorporated by reference), etc.

The compounds of the formula (1-A) or (1-B) wherein $R^1$, $R^2$, $R^3$, $R^4$ and $Y^1$, all have the meanings given above which are preferred examples of the instant compound according to the present invention can be prepared by reacting a compound of the formula (5) with a compound of the formula (6) wherein $Y^1$=lower alkylthio or an acid addition salt thereof.

The acid addition salts of the compound (6) include salts formed from hydrochloric acid, hydrobromic acid, sulfuric acid, etc. The reaction is conveniently carried out in the presence of a solvent. It is often convenient to use conventional solvents which are free from any adverse action on the reaction. Preferred examples of such solvents are acetic acid, ethanol, DMF, etc. The reaction temperature range is about 0 to 200° C. and preferably about 50° C. to reflux.

The compounds of the formula (1-A) and (1-B) according to the present invention are position isomers regarding 3- and 5-substituents on the 1H-pyrazole moiety. Although both compounds are ordinarily obtained in the form of mixtures, they can be resolved each other by a variety of isomer separations conventionally applicable in organic chemical synthesis fields. Representatives of such separations include recrystallization, column chromatography on silica gel, high performance liquid chromatography, thin layer chromatography, and the like.

The compounds of the formula (1-C) and (1-D) wherein $R^1$, $R^2$, $R^3$ and $R^4$, all have the meanings given above and $Y^2$ is lower alkylsulfonyl, which are other preferred examples of the instant compound according to the present invention, can be prepared by the oxidation of the compounds (1-A) and (1-B), respectively. Representative oxidizing agents which can be employed in the reaction include m-chloroperbenzoic acid, OXONE (monopersulfate compound), hydrogen peroxide, periodic acid, and the like. The reaction can be conducted in the presence of or in the absence of a solvent. When the reaction is conducted in solvents, it is often convenient to use conventional solvents which are free from any adverse action on the reaction. Preferred examples of such solvents are methylene chloride, chloroform, acetone, water, etc. The reaction temperature range is about −10 to 100° C. and preferably about 0 to 50° C.

The compounds (1-C) and (1-D) can also be prepared by the oxidation of the mixture of the compounds (1-A) and (1-B) in the same manner as aforementioned, followed by the separation of the resulting mixtures containing the compounds (1-C) and (1-D) as aforementioned.

The compounds of the formula (1-E) wherein $R^1$, $R^2$, $R^3$, $R^4$ and $Y^3$, all have the meanings given above which are other preferred examples of the instant compound according to the present invention can be prepared by reacting a compound of the formula (5) with a compound of the formula (7) wherein $Y^3$=lower alkylsulfonyl or sulfamoyl or an acid addition salt thereof. The reaction can be conducted under conditions similar to those for the reaction between the compound (5) and the compound (6) or an acid addition salt thereof as aforementioned.

Hence, the compounds of the formula (2) which have a benzothiazole moiety on the 5-position of the 1H-pyrazole radical can be prepared according to preparation methods for the compounds (1-A), (1-C) and (1-E) in the scheme given above. Simultaneously, the compounds (1-B) and (1-D) can be obtained as isomers thereof.

The aforementioned preparation processes can be applied to the production of compounds having the formula (1) wherein X=oxygen or NH in the same manner (or in suitably modified manners). For instance, the instant compounds (1) wherein X is NH can be prepared by conducting the preparation processes given above, as required, after protecting one nitrogen atom on the benzimidazole moiety with a protecting group for an amino radical, conventionally employed in the organic chemical synthesis fields, such as benzyl, acyl and alkoxycarbonyl, followed by removal of said protecting group.

Another aspect of the present invention relates to pharmaceutical compositions comprising an effective amount of a compound of the formula (1) or a pharmaceutically acceptable salt thereof in admixture with a pharmaceutically acceptable carrier, including COX-2 inhibitors and anti-inflammatory drugs.

It has been known that there are two isoforms of COX, i.e., COX-1 and COX-2; COX-1 is a constitutive enzyme, which systemically and constantly exists in stomach, kidney, blood platelets, etc., and COX-2 is an inducible enzyme, which is induced at inflamed sites upon inflammation. The compounds of the present invention have potent inhibitory actions on COX-2 while quite weak inhibitory actions on COX-1 systemically and constantly existing in stomach, kidney, etc., thereby facilitating the selective control of biosynthesis of prostaglandins in inflamed sites. Accordingly, the compounds of the present invention are useful as selective COX-2 inhibitors and anti-inflammatory drugs having a reduced potential for adverse effects, such as attacks on gastric mucosa, kidney, etc.

The compounds of the present invention inhibit selectively COX-2, thereby enabling us to control or alleviate inflammation and a variety of symptoms associated therewith, such as edema, tumefaction, ache, pain and fever. In addition, most of the compounds of the present invention are relatively potent analgesics and they may be used not only as anti-inflammatory agents but also as analgesic anti-inflammatory agents. Further, the compounds of the present invention are immunoregulators. Thus, the compounds of the present invention may be useful in the therapeutic and/or prophylactic treatment and/or relief of diseases including inflammation associated immune systems. In an embodiment, the instant compounds wherein a substituent is present on the 4-position of the benzothiazole moiety (for example, Example 6: 4-fluoro-2-[1-(4-methylsulfonylphenyl)-3-trifluoromethyl-1H-pyrazol-5-yl]-benzothiazole) have not only anti-inflammatory actions but also controlling actions in index tests for evaluating immunoregulating activity (III-type allergy: Arthus reaction and IV-type allergy: delayed cutaneous anaphylaxis induced with oxazolone), thereby suggesting that they may be used as immunoregulators. Thus, target diseases to be treated according to the present invention include inflammation and various symptoms associated therewith such as aches and pains. Representative examples of such diseases and symptoms include inflammatory symptoms, aches, pains, swellings, fevers and the like in the following diseases and disorders: chronic rheumatoid arthritis, arthritis associated with other collagen diseases, osteoarthritis, spondylosis deformans, lumbago, tendinitis and tenosynovitis, cervico-omo-brachial syndrome, periarthritis scapulohumeralis, neuralgia, common cold syndrome, oropharyngolaryngitis, bronchitis, afterpains, intrapelvic inflammation, intradorsal inflammation, adnexitis, dysmenorrhea, cystitis, prostatitis, anterior ocular segment inflammation, inflammation after operation, trauma and removal of suture, odontitis, periodontitis, herpes zoster, erythema multiforme exudativum, erythema nodosum, erythema annulare centrifugum, and gouty seizure.

For the foregoing diseases and disorders, the compounds of the present invention can be used independently without any additives, but preferably in admixture with any of pharmaceutically acceptable additives. The compounds of the present invention may be orally, parenterally (including by injection), topically (including ophthalmically, rectally, or cutaneously) administered as pharmaceutical compositions or formulations wherein the topical routes include an application to inflamed sites. One or more components selected from known pharmaceutical additives (hereinafter also referred to "pharmaceutical ingredient(s)") can be employed in the aforementioned pharmaceutical compositions or formulations for any of administration routes.

For oral administration, the aforementioned additives are any pharmaceutical ingredients as long as they are suitable for oral drugs and the intended purposes according to the present invention. Usually, the pharmaceutical additive is selected from conventional pharmaceutical ingredients such as vehicles, binders, disintegrants, lubricants and coating agents. The oral formulations of the present invention include tablets, capsules, granules, fine granules, powders, syrups, etc.

For injection, the additives include pharmaceutical ingredients suitable for aqueous or non-aqueous injections. Usually, the additive is selected from conventional pharmaceutical ingredients such solubilizers, solution adjuvants, suspending agents, buffers (pH regulators), stabilizers and preservatives. In addition, it may be selected from conventional ingredients suitable for preparing powders for injection, which are used in solution or suspension when administered.

For topical application to eye, rectum, skin, etc., the additives include pharmaceutical ingredients suitable for preparing aqueous or non-aqueous solutions, gels or ointments. Usually, the additive is selected from conventional pharmaceutical ingredients such solubilizers, solution adjuvants, suspending agents, buffering agents, stabilizers, preservatives, vaseline, purified lanolin, liquid paraffin, Plastibase (trade name: Squibb & Sons, USA), and Witepsol (trade name: Dynamit Nobel).

Desired oral drugs, injections or drugs for topical applications comprising the compound of the present invention in admixture with the aforementioned ingredient can be prepared according to manufacturing methods known per se, for example, those described in The 13th Pharmacopoeia of Japan (JPXIII) or appropriately modified ones.

The pharmaceutical compositions (drugs) of the present invention are administered to mammals, particularly including human. The doses of these compounds or salts thereof are usually about 5 to 1,000 mg (per day), preferably about 10 to 500 mg (per day) for oral administration; usually about 2 to 200 mg (per day), preferably about 5 to 100 mg (per day) for injection; and usually about 0.5 to 200 mg (per day), preferably about 1 to 100 mg (per day) for topical applications. Specific administration routes and dose levels (including the optimal dose) for any particular patient will be employed depending upon a variety of factors including the patient's conditions (general health, the severity of the particular disease or symptom undergoing therapy, the presence or absence of complications thereof, etc.), the age, sex, body weight, and the like.

ASSAY EXAMPLES

Described below are examples of pharmacological assays for the efficacy and safety of the compounds (1) of the present invention wherein their protocols and results are provided.

Assay Example 1

Inhibitory Activity on COX-1 and COX-2 (1)
<Protocol>

The assays were conducted according to Tanaka et al. method (Jpn. J. Pharmacol., 67, 305–314 (1995)), using, as COX-1 and COX-2, semi-purified enzymes obtained from Cayman Chemical Co. Radioactivity was measured for [$^{14}$C]-prostaglandin E produced from [$^{14}$C]-arachidonic acid, a substrate for the enzyme. Representative results are shown in Table 1. In Table 1, IC$_{50}$ values ($\mu$M) represent the concentration of each test compound required for 50% inhibition of COX-1 or COX-2 activity and COX-1/COX-2 values represent the ratio of IC$_{50}$ values thereof, respectively.

TABLE 1

| | COX Inhibiting Activity IC$_{50}$($\mu$M) | | |
|---|---|---|---|
| Test Compound | COX-1 | COX-2 | COX-1/COX-2 |
| Example 2 | >100 | 0.38 | >263 |
| Example 6 | >100 | 4.3 | >23.3 |
| Example 8 | >100 | 0.34 | >294 |
| Example 10 | >100 | 0.54 | >185 |
| Example 11 | >100 | 0.48 | >208 |
| Example 13 | 47 | 0.33 | 142 |
| SC-58125* | >100 | 0.17–0.47 | >213 |
| YM-177* | 5.2 | 0.049 | 106 |

*SC-58125 = 5-(4-fluorophenyl)-1-(4-methylsulfonylphenyl)-3-trifluoromethyl-1H-pyrazole; YM-177 = 4-[5-(4-methylphenyl)-3-trifluoromethyl-1H-pyrazol-1-yl]benzenesulfonamide \* SC-58125=5-(4-fluorophenyl)-1-(4-methylsulfonylphenyl)-3-trifluoromethyl-1H-pyrazole; YM-177=4-[5-(4-methylphenyl)- 3-trifluoromethyl-1H-pyrazol-1-yl]benzenesulfonamide <Conclusion>

As seen in Table 1, the compounds of the present invention are potent selective inhibitors against COX-2.

Assay Example 2

Inhibitory Action on Adjuvant Arthritis (1)
<Protocol>

Compounds are assayed for actions on rat adjuvant-induced arthritis, according to Theisen-Popp et al. (Agents Actions, 42, 50–55(1994)). Dry Mycobacterium butyricum killed organisms (Difco) were suspended in liquid paraffin to make the concentration 1% and the resulting suspension used as an adjuvant. The adjuvant (50 $\mu$l) was subplantarly injected to the right hind paw of male Fisher rats (5 to 6 animals per group) to raise arthritis. Each test compound was suspended in a 0.5% aqueous sodium carboxymethyl-cellulose (CMC-Na) solution and orally administered to the rats at a dose of 5 mg/kg on days 0, 3, 7, 10, 14, 17 and 20 (7 times in total) after the arthritis induction. On the 21st disease day the rats were measured for their body weight and the edema of their right and left hind paws. Simultaneously, systemic inflammatory states were scored. In addition, each of their spleen and thymus was taken out by excision to measure their wet weight and their relative weight per 100 g body weight was calculated. The results are shown in Table 2.

<Conclusion>

As seen in Table 2, the compounds of the present invention exert potent edema-inhibiting activity in any of inflamed paws and non-inflamed paws and also advantageous inhibitory action in view of systemic inflammatory scores. Further, all the groups receiving the compound of the present invention exhibit good gains in body weight.

Assay Example 3

Analgesic Action in Acetic Acid Writhing
<Protocol>

A 0.7% acetic acid solution was intraperitoneally administered to male ddY mice at a dose of 10 ml/kg body weight. The frequency of writhing manifested was counted as an index of pains for a period of 10 minutes starting from the 10th minute after the administration. Ten or thirty minutes prior to the acetic acid administration, each test compound was orally given. The results are shown in Table 3.

TABLE 3

| | | % Inhibition of Writhing Response | |
|---|---|---|---|
| Test Compound | Dose (mg/kg) | Administration Point 1)* | Administration Point 2)* |
| Example 2 | 10 | 49 | 57 |
| SC-58125 | 30 | 22 | |
| YM-177 | 30 | | 17 |
| Indomethacin | 3 | | 28 |

*Administration Point 1) = Oral application of each test compound 10 minutes prior to acetic acid-administration
*Administration Point 2) = Oral application of each test compound 30 minutes prior to acetic acid-administration <Conclusion>

As seen in Table 3, the compounds of the present invention exert potent analgesic activity.

Assay Example 4

Toxicology Study
<Protocol>

Tests were carried out in a dose-increasing manner. Male ICR mice (5-week-old) were pre-fed for 10 days and then assigned to groups (a control group, a group administered with the compound of the present invention (present invention compound-administered group), and a YM-177-administered group; 5 animals per group). Each test compound was suspended in a 0.5% aqueous CMC-Na solution and given to the mice successively at a dose of 125 mg/kg

TABLE 2

| | % Inhibition against | Edema Inhibition (%) | | Inflammation | % Inhibition against Change in Relative Weight | |
|---|---|---|---|---|---|---|
| | Reduction of Gain in | Left Hind Paw (Non-inflamed | Right Hind Paw (Inflamed | Score Inhibition | | |
| Test Compound | Body Weight | Paw) | Paw) | (%) | Thymus | Spleen |
| Example 2 | 75.9 | 91 | 94 | 97 | 56.7 | 2.5 |
| Example 4 | 78.7 | 91 | 83 | 100 | 148.9 | 2.9 |
| Example 6 | 104.6 | 105 | 84 | 97 | 130.3 | 42.6 |
| Example 13 | 48.6 | 76 | 71 | 78 | 71.3 | −10.5 |
| SC-58125 | 96.9 | 95 | 76 | 96 | 111.2 | 11.9 |
| YM-177 | 25.5 | 65 | 37 | 44 | 33.7 | −19.7 |
| Indomethacin | 19.8 | 75 | 43 | 51 | −75.8 | −45.3 | on the first day, at a dose of 250 mg/kg on the second day, at a dose of 500 mg/kg on the third day, and at a dose of 1,000 mg/kg on the fourth day. The control group received a 0.5% aqueous CMC-Na solution at a dose of 10 ml/kg. Daily from the initial administration to the fifth day, the mice were observed whether dead or alive. Simultaneously, the body weight was also measured.

<Conclusion>

None of animals were died in every group when the test compounds were administered. In addition, body weight changes in both the present invention compound- and YM-177-administered groups were similar to those in the control group. Accordingly, no toxic signs were found.

Assay Example 5

Inhibitory Activity on COX-1 and COX-2 (2)

<Protocol>

In the same manner as for the above Assay Example 1, the compounds of the present invention and control compound (indomethacin) were assayed for $IC_{50}$ values against COX-1 and COX-2, respectively, and their IC ratios calculated. The results are shown in Table 4.

TABLE 4

| | COX Inhibiting Activity $IC_{50}(\mu M)$ | | |
|---|---|---|---|
| Test Compound | COX-1 | COX-2 | COX-1/COX-2 |
| Example 14 | >100 | 0.056 | >1786 |
| Example 16 | >100 | 0.58 | >172 |
| Example 17 | >100 | 0.16 | >625 |
| Example 18 | >100 | 0.16 | >625 |
| Example 21 | 22 | 0.057 | 386 |
| Example 22 | >100 | 0.05 | >2000 |
| Example 23 | >100 | 0.11 | >909 |
| Example 24 | 1.8 | 0.086 | 21 |
| Example 25 | >100 | 0.4 | >250 |
| Example 26 | >100 | 0.13 | >769 |
| Example 27 | 33 | 0.053 | 623 |
| Example 28 | >100 | 0.084 | >1190 |
| Example 29 | >100 | 0.012 | >8333 |
| Example 31 | >100 | 0.24 | >417 |
| Example 32 | >100 | 0.37 | >270 |
| Example 33 | >100 | 0.13 | >769 |
| Example 41 | >100 | 0.24 | >417 |
| Indomethacin | 0.12–0.42 | 0.22–2.1 | — |

<Conclusion>

As seen in Table 4, the compounds of the present invention are potent selective inhibitors against COX-2.

Assay Example 6

Inhibitory Action on Adjuvant Arthritis (2)

<Protocol>

A 1% dry Mycobacterium tuberculosis H37 RA killed organism suspension in liquid paraffin was employed as an adjuvant. The adjuvant suspension (50 μl) was subplantarly administered to the right hind paw of male F344/Du (Fisher) rats (5 to 6 animals per group) to raise arthritis. Each test compound was suspended in a 0.5% aqueous CMC-Na solution and orally administered to the rats at a dose of 1 mg/5 ml/kg daily for 17 consecutive days starting from the arthritis-induced day. The next day after the final administration, the rats were measured for their body weight and the edema of their right and left hind paws. Simultaneously, systemic inflammatory states were scored. In addition, each of their spleen and thymus was taken out by excision to measure their wet weight and their relative weight per 100 g body weight was determined. The results are shown in Table 5.

TABLE 5

| | % Inhibition against Reduction of Gain in Body Weight | Edema Inhibition (%) | | Inflammation Score Inhibition (%) | % Inhibition against Change in Relative Weight | |
|---|---|---|---|---|---|---|
| | | Left Hind Paw (Non-inflamed Paw) | Right Hind Paw (Inflamed Paw) | | Thymus | Spleen |
| Test Compound | | | | | | |
| Example 18 | 75 | 116 | 84 | 91 | 48 | 48 |
| Example 29 | 73 | 124 | 82 | 86 | 80 | 25 |
| YM-177 | 21 | 60 | 41 | 49 | 59 | 15 |

<Conclusion>

As seen in Table 5, the compounds of the present invention exert potent edema-inhibiting activity in any of inflamed paws and non-inflamed paws and also advantageous inhibitory action in view of systemic inflammatory scores. Further, all the groups receiving the compound of the present invention exhibit good gains in body weight during the assays.

Assay Example 7

Inhibitory Action on Arthus Reaction

<Protocol>

Rat anti-ovalbumin serum was prepared by the method given below. One mg of ovalbumin was dissolved in 1 ml of physiological saline and divided to two aliquots. The ovalbumin solution was intramuscularly administered to the femoral portion of male SD rats. Simultaneously, 0.5 ml of 0.05% Mycobacterium butyricum suspension as a Freund's complete adjuvant was intraperitoneally administered to the rats. Three days later, the same treatments were repeated. On the 12th day after the initial sensitization, antisera were collected.

Arthus reaction was induced by intravenuously administering ovalbumin to male SD rats (4 animals per group) at a dose of 0.5 mg/ml/rat immediately followed by subplantar administration of 100 a 1 of rat anti-ovalbumin serum to the left hind paw thereof. Two hours later, the left hind paw volume was measured using a plethysmometer and the increases in paw volume were determined by comparing with those prior to the Arthus reaction induction. For the assays, the compound of the present invention (Example 6 compound) was used at a dose of 50 mg/kg and a control compound (prednisolone) at a dose of 10 mg/kg. Each compound was suspended in a 0.5% aqueous CMC-Na solution and orally administered one hour prior to the ovalbumin administration. Control groups received only a 0.5% aqueous CMC-Na solution. The test of significance was conducted by Dunnett's multiple range test.

<Result>

The control-group increase in edematized left hind paw volume is (0.74±0.06) ml while the present invention compound-group (0.54±0.04) ml with 27% edema inhibition and the prednisolone-group (0.51±0.02) ml with 31% edema inhibition, whereby it is found that their edema-inhibiting actions are significant with not more than 1% error level.

From the foregoing, the compounds of the present invention exert potent inhibiting activity on Arthus reaction (immediate III-type allergy) which is an index test for evaluating immunoregulating actions.

Assay Example 8

Inhibitory Action on Oxazolone-Induced Dermal Delayed Type Hypersensitivity

<Protocol>

Sensitization was conducted by topically applying 150 $\mu$l of 1% oxazolone solution (ethanol:acetone=3:1) to mice (5 to 6 animals per group), the abdominal and pectral regions of which were shaved in advance. Four days after the sensitization, 10 $\mu$l of 0.8% oxazolone solution (in olive oil) was topically applied to the rat left auricle to raise the response. Twenty-four hours later the auricular thickness was measured using a dial-gauge (Mitsutoyo Co.). Values obtained by subtracting auricular thickness data prior to the challenge were taken as indexes of the response. For the assays, the compound of the present invention (Example 6 compound) was used at a dose of 30 mg/kg and the control compound (prednisolone) at a dose of 10 mg/kg. Each test compound was suspended in a 0.5% aqueous CMC-Na solution and orally administered daily for 4 consecutive days from the next day after the sensitization. One hour after the final administration, the challenge was conducted. Control groups received only a 0.5% aqueous CMC-Na solution.

<Result>

The control-group increase in mouse edematized auricle thickness is (0.12±0.03) mm while the present invention compound-group (0.06±0.01) mm with 48% edema inhibition and the prednisolone-group (0.04±0.01) mm with 70% edema inhibition.

From the foregoing, the compounds of the present invention exert potent inhibiting activity on oxazolone-induced dermal delayed type hypersensitivity (IV-type allergy involved with cellular immunity) which is an index test for evaluating immunoregulating actions.

EXAMPLES

Described below are examples of the present invention which are provided only for illustrative purposes, and not to limit the scope of the present invention. In light of the present disclosure, numerous embodiments within the scope of the claims will be apparent to those of ordinary skill in the art.

Example 1

6-Fluoro-2-[1-(4-methylthiophenyl)-3-trifluoromethyl-1H-pyrazol-5-yl]benzothiazole and 6-fluoro-2-[1-(4-methylthiophenyl)-5-trifluoromethyl-1H-pyrazol-3-yl]benzothiazole 1) To a suspension of sodium methoxide (0.581 mg, 1.08 mmol) in THF (15 ml) was added a solution of ethyl trifluoroacetate (1.456 g, 10.2 mmol) in THF (7 ml) under nitrogen atmosphere. To the resulting mixture was added a solution of 2-acetyl-6-fluorobenzothiazole (2.00 g, 10.2 mmol) in THF (25 ml) dropwise along with ice cooling. The mixture was stirred at room temperature for 1.5 hours, and then concentrated. The resultant residue was subjected to purification using column chromatography on silica gel to afford 1-(6-fluorobenzothiazol-2-yl)-4,4,4-trifluorobutane-1,3-dione (1.26 g, 42%). NMR(CDCl$_3$-DMSO-d$_6$) $\delta$: 6.85 (1H, s), 7.23 (1H, app dt, J=2.6 Hz, 8.9 Hz), 7.59 (1H, dd, J=2.6 Hz, 8.2 Hz), 8.05 (1H, dd, J=4.6 Hz, 8.9 Hz); mp 175–178° C.

2) The mixture of 1-(6-fluorobenzothiazol-2-yl)-4,4,4-trifluorobutane-1,3-dione (820 mg, 2.82 mmol) and 4-methylthio-phenylhydrazine (529.5 mg, 3.43 mmol) in acetic acid (23 ml) was stirred at 100° C. for 13 hours, allowed to cool and then concentrated. The resulting residue was subjected to purification using column chromatography on silica gel to afford 6-fluoro-2-[1-(4-methylthiophenyl)-3-trifluoromethyl-1H-pyrazol-5-yl]benzothiazole (500 mg, 43%) and 6-fluoro-2-[1-(4-methylthiophenyl)-5-trifluoromethyl-1H-pyrazol-3-yl]-benzothiazole (58 mg, 5%).

6-Fluoro-2-[1-(4-methylthiophenyl)-3-trifluoromethyl-1H-pyrazol-5-yl]benzothiazole: NMR(CDCl$_3$) $\delta$: 2.55 (3H, s), 7.28 (1H, app dt, J=2.6 Hz, 8.9 Hz), 7.32 (1H, s), 7.31–7.44 (4H, m), 7.50 (1H, dd, J=2.6 Hz, 7.9 Hz), 7.98 (1H, dd, J=4.6 Hz, 8.9 Hz); mp 135–137° C.

6-Fluoro-2-[1-(4-methylthiophenyl)-5-trifluoromethyl-1H-pyrazol-3-yl]benzothiazole: NMR(CDCl$_3$) $\delta$: 2.56 (3H, s), 7.25 (1H, app dt, J=2.6 Hz, 8.9 Hz), 7.34–7.53 (4H, m), 7.51 (1H, s), 7.61 (1H, dd, J=2.6 Hz, 8.2 Hz), 8.03 (1H, dd, J=4.6 Hz, 8.9 Hz); mp 195–196° C.

Example 2

6-Fluoro-2-[1-(4-methylsulfonylphenyl)-3-trifluoromethyl-1H-pyrazol-5-yl]benzothiazole To a solution of 6-fluoro-2-[1-(4-methylthiophenyl)-3-trifluoromethyl-1H-pyrazol-5-yl]benzothiazole (20 mg, 0.5 mmol) in methylene chloride (1 ml) was added a solution of 70% m-chloroperbenzoic acid (24 mg) in methylene chloride (1 ml) dropwise while ice cooling and the mixture was stirred for one hour. The reaction mixture was diluted with methylene chloride and washed successively with water, sodium bicarbonate and water. The organic layer was dried over magnesium sulfate, and then evaporated. The resulting residue was subjected to recrystallization from isopropyl ether to afford 6-fluoro-2-[1-(4-methylsulfonylphenyl)-3-trifluoromethyl-1H-pyrazol-5-yl]-benzothiazole (15 mg, 69%). NMR(CDCl$_3$) $\delta$: 3.11 (3H, s), 7.23 (1H, app dt, J=2.6 Hz, 8.9 Hz), 7.58 (1H, dd, J=2.3 Hz, 7.69 Hz), 7.72–8.10 (4H, m), 7.90 (1H, dd, J=4.6 Hz, 8.9 Hz); mp 194–196° C.

Example 3

5-Fluoro-2-[1-(4-methylthiophenyl)-3-trifluoromethyl-1H-pyrazol-5-yl]benzothiazole and 5-fluoro-2-[1-(4-methylthiophenyl)-5-trifluoromethyl-1H-pyrazol-3-yl]benzothiazole 1) The procedure of Example 1 was repeated using 2-acetyl-5-fluorobenzothiazole as the starting material to obtain the following product: 1-(5-fluorobenzothiazol-2-yl)-4,4,4-trifluorobutane-1,3-dione: NMR(CDCl$_3$-DMSO-d$_6$) $\delta$: 6.77 (5H, s), 7.22 (4H, app dt, J=2.6 Hz, 8.9 Hz), 7.76 (1H, dd, J=2.3 Hz, 9.6 Hz), 7.87 (1H, dd, J=5.1 Hz, 8.9 Hz)

2) The above product compound was treated with 4-methylthio-phenyl hydrazine according to the procedure for Example 1 to give the following products:

5-Fluoro-2-[-(4-methylthiophenyl))-3-trifluoromethyl-1H-pyrazol-5-yl]benzothiazole: NMR(CDCl$_3$) $\delta$: 2.55 (3H, s), 7.20 (1H, app dt, J=2.6 Hz, 8.9 Hz), 7.33 (1H,s), 7.32–7.44 (4H, m), 7.70 (1H, dd, J=2.6 Hz, 9.2 Hz), 7.74 ((H, dd, J=5.3 Hz, 8.9 Hz); mp 168–169° C.

5-Fluoro-2-[1-(4-methylthiophenyl)-5-trifluoromethyl-1H-pyrazol-3-yl]benzothiazole: NMR(CDCl$_3$) $\delta$: 2.56 (3H, s), 7.25 (1H, app dt, J=2.6 Hz, 8.9 Hz), 7.33–7.52 (4H, m), 7.53 (4H, m), 7.76 (1H, dd, J=2.6 Hz, 9.6 Hz), 7.85 (1H, dd, J=5.0 Hz, 8.9 Hz); mp 210–211° C.

Example 4

5-Fluoro-2-[1-(4-methylsulfonylphenyl)-3-trifluoromethyl-1H-pyrazol-5-yl]benzothiazole The procedure of Example 2 was repeated using 5-fluoro-2-1-(4-methylthiophenyl )-3-trifluoromethyl-(H-pyrazol-5-yl]-benzothiazole (401 mg, 0.98 mmol). The resulting product was subjected to recrystallization from ethyl acetate and isopropyl ether to afford 5-fluoro-2-[1-(4-methylsulfonylphenyl)- 3-trifluoromethyl-1H-pyrazol-5-yl]benzothiazole (358 mg, 83%) as a white crystal.

NMR(CDCl$_3$) δ:3.12(3H, s), 7.27 (1H, dd, J=2.3 Hz, 8.9 Hz), 7.63 (1H, dd, J=2.3 Hz, 8.9 Hz), 7.73–8.09 (4H, m), 7.84 (1H, dd, J=4.9 Hz, 8.9 Hz); mp 204–205° C.

Example 5

4-Fluoro-2-[1-(4-methylthiophenyl)-3-trifluoromethyl-1H-pyrazol-5-yl]benzothiazole 1) The procedure of Example 1 was repeated using 2-acetyl-4-fluorobenzothiazole as the starting material to obtain the following product:

1-(4-fluorobenzothiazol-2-yl)-4,4,4-trifluorobutane-1,3-dione: NMR(CDCl$_3$-DMSO-d$_6$) δ: 6.88 (1H, s), 7.13–7.23 (1H, m), 7.38 (1H, dt, J=4.6 Hz, 7.9 Hz), 7.65 (1H, app d, J=7.3 Hz)

2) The above product compound was treated with 4-methylthio-phenylhydrazine according to the procedure for Example 1 to give 4-fluoro-2-[1-(4-methylthiophenyl)-3-trifluoromethyl-1H-pyrazol-5-yl]benzothiazole:

NMR(CDCl$_3$) δ: 2.55 (3H, s), 7.18–7.25 (1H, m), 7.33–7.45 (4H, m), 7.36 (1H, s), 7.38–7.60 (2H, m)

Example 6

4-Fluoro-2-[1-(4-methylsulfonylphenyl)-3-trifluoromethyl-1H-pyrazol-5-yl]benzothiazole The oxidation procedure of Example 2 was repeated using 4-fluoro-2-[1-(4-methylthiophenyl)-3-trifluoromethyl-1H-pyrazol-5-yl]benzothiazole obtained in Example 5-2) to obtain 4-fluoro-2-[1-(4-methylsulfonylphenyl)-3-trifluoromethyl-1H-pyrazol-5-yl]benzothiazole.

NMR(CDCl$_3$) δ: 3.12 (3H, s), 7.18–7.26 (1H, m), 7.31 (1H, s), 7.43 (1H, dt, J=4.6 Hz, 8.1 Hz), 7.67 (1H, app d, J=8.3 Hz), 7.76–8.10 (4H, m); mp 208–209° C.

Example 7

2-[1-(4-Methylthiophenyl)-3-trifluoromethyl-1H-pyrazol-5-yl]-benzothiazole

1) The procedure of Example 1 was repeated using 2-acetyl-benzothiazole as the starting material to obtain the following product:

1-(benzothiazol-2-yl)-4,4,4-trifluorobutane-1,3-dione: NMR(CDCl$_3$-DMSO-d$_6$) δ: 6.73 (1H, s), 7.40–7.60 (2H, m), 7.96–8.15 (2H, m)

2) The above product compound was treated with 4-methylthio-phenylhydrazine according to the procedure for Example 1 to give 2-[1-(4-methylthiophenyl)-3-trifluoromethyl-1H-pyrazol-5-yl]benzothiazole:

NMR(CDCl$_3$) δ: 2.55 (3H, s), 7.31–7.44 (4H, m), 7.32–7.54 (3H, m), 7.83 (1H, app d, J=8.6 Hz), 8.03 (1H, app d, J=7.6 Hz)

Example 8

2-[1-(4-Methylsulfonylphenyl)-3-trifluoromethyl-1H-pyrazol-5-yl]benzothiazole

The oxidation procedure of Example 2 was repeated using 2-[1-(4-methylthiophenyl)-3-trifluoromethyl-1H-pyrazol-5-yl]benzothiazole obtained in Example 7-2) to obtain 2-[1-(4-methylsulfonylphenyl)-3-trifluoromethyl-1H-pyrazol-5-yl]benzothiazole.

NMR(CDCl$_3$) δ: 3.11 (3H, s), 7.26 (1H, s), 7.44–7.57 (2H, m), 7.74–8.08 (4H, m), 7.89–7.98 (2H, m)

Example 9

6-Methoxy-2-[1-(4-methylsulfonylphenyl)-3-trifluoromethyl-1H-pyrazol-5-yl]benzothiazole The mixture of 4,4,4-trifluoro-1-(6-methoxybenzothiazol-2-yl)butane-1,3-dione (300 mg, 1.0 mmol) and 4-methylsulfonyl-phenylhydrazine hydrochloride (260 mg, 1.1 mmol) was heated under reflux in ethanol (50 ml) for 3.5 hours, and then allowed to cool. The precipitated crystals were collected and subjected to recrystallization from ethanol and ethyl acetate-isooctane to afford 6-methoxy-2-[1-(4-methylsulfonylphenyl)-3-trifluoromethyl-1H-pyrazol-5-yl]benzothiazole (350 mg, 77%). NMR(CDCl$_3$) δ: 3.11 (3H, s), 3.89 (3H, s), 7.11 (1H, dd, J=2.3 Hz, 8.6 Hz), 7.20 (1H, s), 7.32 (1H, d, J=2.3 Hz), 7.75 (2H, d, J=8.6 Hz), 7.82 (1H, d, J=8.6 Hz), 8.04 (2H, d, J=8.6 Hz); mp 217–218° C.

Example 10

6-Chloro-2-[1-(4-methylsulfonylphenyl)-3-trifluoromethyl-1H-pyrazol-5-yl]benzothiazole The procedure of Example 9 was repeated using 4,4,4-trifluoro-1-(6-chlorobenzothiazol-2-yl)butane-1,3-dione as the starting material to obtain 6-chloro-2-[1-(4-methylsulfonyl-phenyl)-3-trifluoromethyl-1H-pyrazol-5-yl]benzothiazole. NMR(CDCl$_3$) δ: 3.11(3H, s), 7.26(1H, s), 7.48(1H, dd, J=2.3 Hz, 9.0 Hz), 7.73–7.89(4H, m), 8.06(2H, d, J=8.5 Hz); mp 195–196° C. (ethanol)

Example 11

4-[5-(6-Methoxybenzothiazol-2-yl)-3-trifluoromethyl-1H-pyrazol-1-yl]benzenesulfonamide The procedure of Example 9 was repeated using 4,4,4-trifluoro-1-(6-methoxybenzothiazol-2-yl)butane-1,3-dione and 4-sulfamoylphenylhydrazine hydrochloride as the starting materials to obtain 4-[5-(6-methoxybenzothiazol-2-yl)-3-trifluoromethyl-1H-pyrazol-1-yl]benzenesulfonamide. NMR(CDCl$_3$) δ: 3.88 (3H, s), 5.03 (2H, bs), 7.11 (1H, dd, J=2.3 Hz, 8.9 Hz), 7.20 (1H, s), 7.31 (2H, d, J=2.3 Hz), 7.68 (2H, d, J=8.6 Hz), 7.83 (1H, d, J=8.9 Hz), 8.01 (2H, d, J=8.6 Hz); mp 236–237° C. (ethyl acetate-isooctane)

Example 12

4-[5-(6-Chlorobenzothiazol-2-yl)-3-trifluoromethyl-1H-pyrazol-1-yl]benzenesulfonamide The procedure of Example 9 was repeated using 4,4,4-trifluoro-1-(6-chlorobenzothiazol-2-yl)butane-1,3-dione and 4-sulfamoylphenylhydrazine hydrochloride as the starting materials to obtain 4-[5-(6-chlorobenzothiazol-2-yl)-3-trifluoromethyl-1H-pyrazol-1-yl]benzenesulfonamide. NMR(CDCl$_3$-DMSO-d$_6$) δ: 6.91 (2H, bs), 7.30–7.49 (2H, m), 7.63 (2H, d, J=8.9 Hz), 7.88–7.91 (2H, m), 8.05 (2H, d, J=8.9 Hz); mp 254–255° C. (ethanol)

Example 13

4-[5-(6-Fluorobenzothiazol-2-yl)-3-trifluoromethyl-1H-pyrazol-1-yl]benzenesulfonamide The mixture of 4,4,4-trifluoro-1-(6-fluorobenzothiazol-2-yl)butane-1,3-dione (800 mg, 2.7 mmol) and 4-sulfamoylphenyl-hydrazine (720 mg, 3.8 mmol) was heated under reflux in acetic acid (10 ml) for 16 hours. After cooling, the reaction mixture was poured into water and extracted with methylene chloride. The organic layer was washed with water, dried over magnesium sulfate, and then evaporated. The residue was subjected to purification using chromatography on silica gel to afford 4-[5-(6-fluorobenzothiazol-2-yl)-3-trifluoromethyl-1H-pyrazol-1-yl]benzenesulfonamide (510 mg, 42%) as a colorless needle. NMR(CDCl$_3$-DMSO-d$_6$) δ: 6.70 (2H, bs), 7.22–7.39 (2H, m), 7.57–7.67 (3H, m), 7.91–7.96 (1H, m), 8.05 (2H, d, J=8.6 Hz); mp 260–261° C. (toluene)

Example 14
4-[5-(Benzothiazol-2-yl)-3-trifluoromethyl-1H-pyrazol-1-yl]-benzenesulfonamide The product obtained in Example 7.1), 1-(benzothiazol-2-yl)-4,4,4-trifluorobutane-1,3-dione, was treated with 4-sulfamoylphenylhydrazine hydrochloride in the same manner as in Example 9 to give 4-[5-(benzothiazol-2-yl)-3-trifluoromethyl-1H-pyrazol-1-yl]benzenesulfonamide (yield, 44%).

NMR(CDCl$_3$-DMSO-d$_6$) δ: 7.17 (2H, s), 7.33 (1H, s), 7.45–7.68 (4H, m), 7.92–8.08 (4H, m); mp 254–256° C. (DMF-ethanol)

Example 15
6-Methyl-2-[1-(4-methylsulfonylphenyl)-3-trifluoromethyl-1H-pyrazol-5-yl]benzothiazole The procedure of Example 9 was repeated using 1-(6-methylbenzothiazol-2-yl)-4,4,4-trifluorobutane-1,3-dione and 4-methylsulfonylphenylhydrazine hydrochloride as the starting materials to obtain 6-methyl-2-[1-(4-methylsulfonylphenyl)-3-trifluoromethyl-1H-pyrazol-5-yl]benzothiazole (yield, 47%).

NMR(CDCl$_3$) δ: 2.51 (3H, s), 3.10 (3H, s), 7.22 (1H, s), 7.52 (1H, d, J=8.2 Hz), 7.69 (1H, s), 7.73–7.76 (3H, m), 7.83 (1H, d, J=8.2 Hz), 8.04(2H, d, J=8.9 Hz); mp 202.5–203.5° C. (ethanol)

Example 16
4-[5-(6-Methylbenzothiazol-2-yl)-3-trifluoromethyl-1H-pyrazol-5-yl]benzenesulfonamide The procedure of Example 9 was repeated using 1-(6-methylbenzothiazol-2-yl)-4,4,4-trifluorobutane-1,3-dione and 4-sulfamoylphenylhydrazine hydrochloride as the starting materials to obtain 4-[5-(6-Methylbenzothiazol-2-yl)-3-trifluoromethyl-1H-pyrazol-5-yl]benzenesulfonamide (yield, 36%) NMR(CDCl$_3$-DMSO-d$_6$) δ: 2.50 (3H, s), 6.63 (2H, s), 7.32 (1H, d, J=8.5 Hz), 7.39 (1H, s), 7.63 (2H, d, J=8.6 Hz), 7.68 (1H, S), 7.84 (1H, d, J=8.5 Hz), 8.03 (2H, d, J=8.6 Hz); mp 257–258° C. (ethanol)

Example 17
7-Fluoro-2-[1-(4-methylsulfonyl)-3-trifluoromethyl-1H-pyrazol-5-yl]benzothiazole The procedure of Example 9 was repeated using 1-(7-fluorobenzothiazol-2-yl)-4,4,4-trifluorobutane-1,3-dione and 4-methylsulfonylphenylhydrazine hydrochloride as the starting materials to obtain 7-fluoro-2-[1-(4-methylsulfonylphenyl)-3-trifluoromethyl-1H-pyrazol-5-yl]benzothiazole (yield, 38%).

NMR(CDCl$_3$) δ: 3.11 (3H, s), 7.19 (1H, app t, J=8.3 Hz), 7.28 (1H, s), 7.49 (1H, dt, J=5.3 Hz, 8.3 Hz), 7.73–7.78 (3H, m), 8.04–8.05 (2H, m); mp 186.5–187.5° C. (methanol-water)

Example 18
4-[5-(7-Fluorobenzothiazol-2-yl)-3-trifluoromethyl-1H-pyrazol-1-yl]benzenesulfonamide The procedure of Example 9 was repeated using 1-(7-fluorobenzothiazol-2-yl)-4,4,4-trifluorobutane-1,3-dione and 4-sulfamoylphenylhydrazine hydrochloride as the starting materials to obtain 4-[5-(7-fluorobenzothiazol-2-yl)-3-trifluoromethyl-1H-pyrazol-1-yl]benzenesulfonamide (yield, 88%).

NMR(DMSO-d$_6$) δ: 7.46 (1H, app t, J=8.3 Hz), 7.59 (2H, bs), 7.61 (1H, dt, J=5.6 Hz, 8.3 Hz), 7.82–7.85 (1H, m), 7.83–7.86 (2H, m), 7.91(1H, s), 7.96–8.00 (2H, m); mp 251–253° C. (methanol-water)

Example 19
6-Fluoro-5-methyl-2-[1-(4-methylsulfonylphenyl)-3-trifluoromethyl-1H-pyrazol-5-yl]benzothiazole The procedure of Example 9 was repeated using 1-(6-fluoro-5-methylbenzothiazol-2-yl)-4,4,4-trifluorobutane-1,3-dione and 4-methylsulfonylphenylhydrazine hydrochloride as the starting materials to obtain 6-fluoro-5-methyl-2-[1-(4-methylsulfonylphenyl)-3-trifluoromethyl-1H-pyrazol-5-yl]-benzothiazole (yield, 41%).

NMR(CDCl$_3$) δ: 2.40–2.41 (3H, m), 3.11 (3H, s), 7.21 (1H, s), 7.50–7.53 (2H, m), 7.72–7.77 (3H, m), 8.03–8.08 (2H, m); mp 193–194° C. (ethanol)

Example 20
4-[5-(6-Fluoro-5-methylbenzothiazol-2-yl)-3-trifluoromethyl-1H-pyrazol-5-yl]benzenesulfonamide The procedure of Example 9 was repeated using 1-(6-fluoro-5-methylbenzothiazol-2-yl)-4,4,4-trifluorobutane-1,3-dione and 4-sulfamoylphenylhydrazine hydrochloride as the starting materials to obtain 4-[5-(6-fluoro-5-methylbenzothiazol-2-yl)-3-trifluoromethyl-1H-pyrazol-5-yl]benzenesulfonamide (yield, 33%).

NMR(DMSO-d$_6$) δ: 2.35 (3H, m), 7.58 (1H, s), 7.79–8.06 (7H, m); mp 224–225° C. (ethanol)

Example 21
4-[5-(Benzothiazol-2-yl)-3-difluoromethyl-1H-pyrazol-1-yl]-benzenesulfonamide The procedure of Example 9 was repeated using 1-(benzothiazol-2-yl)-4,4-difluorobutane-1,3-dione and 4-sulfamoylphenylhydrazine hydrochloride as the starting materials to obtain 4-[5-(benzothiazol-2-yl)-3-difluoromethyl-1H-pyrazol-1-yl]benzenesulfonamide (yield, 37%). NMR(CDCl$_3$-DMSO-d$_6$) δ: 6.86 (1H, t, J=54.5 Hz), 7.12 (2H, s), 7.25 (1H, s), 7.43–7.66 (4H, m), 7.92–8.06 (4H, m); mp 247–249° C. (DMF-ethanol)

Example 22
6-Fluoro-2-[1-(4-methylsulfonylphenyl)-3-difluoromethyl-1H-pyrazol-5-yl]benzothiazole The procedure of Example 9 was repeated using 1-(6-fluorobenzothiazol-2-yl)-4,4-difluorobutane-1,3-dione and 4-methylsulfonylphenylhydrazine hydrochloride as the starting materials to obtain 6-fluoro-2-[1-(4-methylsulfonylphenyl)-3-difluoromethyl-1H-pyrazol-5-yl]benzothiazole (yield, 65%). NMR(DMSO-d$_6$) δ: 3.30 (3H, s), 7.23 (1H, t, J=54.1 Hz), 7.38–7.46 (1H, m), 7.56 (1H, s), 7.83–7.88 (2H, m), 7.94–7.99 (1H, m), 8.05–8.13 (3H, m); mp 204–206° C. (ethanol)

Example 23
4-[5-(6-Fluorobenzothiazol-2-yl)-3-difluoromethyl-1H-pyrazol-1-yl]benzenesulfonamide The procedure of Example 9 was repeated using 1-(6-fluorobenzothiazol-2-yl)-4,4-difluorobutane-1,3-dione and 4-sulfamoylphenylhydrazine hydrochloride as the starting materials to obtain 4-[5-(6-fluorobenzothiazol-2-yl)-3-difluoromethyl-1H-pyrazol-1-yl]benzenesulfonamide (yield, 57%). NMR(DMSO-d$_6$) δ:7.22 (1H, t, J=54.1 Hz), 7.39–7.47 (1H, m), 7.53 (1H, s), 7.56 (2H, brs), 7.75–7.80 (2H, m), 7.93–8.00 (3H, m), 8.09–8.13 (1H, m); mp 255° C. (ethanol-water)

Example 24
4-[5-(6-Chlorobenzothiazol-2-yl)-3-difluoromethyl-1H-pyrazol-1-yl]benzenesulfonamide The procedure of Example 9 was repeated using 1-(6-chlorobenzothiazol-2-yl)-4,4-difluorobutane-1,3-dione and 4-sulfamoylphenylhydrazine hydrochloride as the starting materials to obtain 4-[5-(6-chlorobenzothiazol-2-yl)-3-difluoromethyl-1H-pyrazol-1-yl]benzenesulfonamide. NMR(DMSO-$d_6$) δ: 7.23 (1H, t, J=54.1 Hz), 7.56 (2H, bs), 7.57 (1H, s), 7.56–7.60 (1H, m), 7.76–7.80 (2H, m), 7.93–7.97 (3H, m), 8.36 (1H, d, J=2.3 Hz); mp 242–244° C. (toluene)

Example 25
4-[3-Difluoromethyl-5-(6-methoxybenzothiazol-2-yl)-1H-pyrazol-5-yl]benzenesulfonamide The procedure of Example 9 was repeated using 1-(6-methoxybenzothiazol-2-yl)-4,4-difluorobutane-1,3-dione and 4-sulfamoylphenylhydrazine hydrochloride as the starting materials to obtain 4-[3-difluoromethyl-5-(6-methoxybenzothiazol-2-yl)-1H-pyrazol-5-yl]benzenesulfonamide (yield, 15%).

NMR(DMSO-$d_6$) δ: 3.83 (3H, s), 7.21 (1H, t, J=54.1 Hz), 7.13 (1H, dd, J=2.6, 8.9 Hz), 7.46 (1H, s), 7.56 (2H, s), 7.74–7.77 (3H, m), 7.83 (1H, d, J=8.9 Hz), 7.94 (2H, d, J=8.6 Hz); mp 211–212° C. (ethanol)

Example 26
6-Methyl-2-[1-(4-methylsulfonylphenyl)-3-difluoromethyl-1H-pyrazol-5-yl]benzothiazole The procedure of Example 9 was repeated using 1-(6-methylbenzothiazol-2-yl)-4,4-difluorobutane-1,3-dione and 4-methylsulfonylphenylhydrazine hydrochloride as the starting materials to obtain 6-methyl-2-[1-(4-methylsulfonylphenyl)-3-difluoromethyl-1H-pyrazol-5-yl]benzothiazole (yield, 84%). NMR(CDCl$_3$) δ: 2.51 (3H, s), 3.10 (3H, s), 6.80 (1H, t, J=54.8 Hz), 7.19 (1H, s), 7.33 (1H, app d, J=8.3 Hz), 7.68 (1H, bs), 7.71–7.74 (2H, m), 7.81 (1H, d, J=8.6 Hz), 8.01–8.04 (2H, m); mp 183–184° C. (ethanol)

Example 27
4-[3-Difluoromethyl-5-(6-methylbenzothiazol-2-yl)-1H-pyrazol-5-yl]benzenesulfonamide The procedure of Example 9 was repeated using 1-(6-methylbenzothiazol-2-yl)-4,4-difluorobutane-1,3-dione and 4-sulfamoylphenylhydrazine hydrochloride as the starting materials to obtain 4-[3-difluoromethyl-5-(6-methylbenzothiazol-2-yl)-1H-pyrazol-5-yl]benzenesulfonamide. NMR(DMSO-$d_6$) δ: 2.45 (3H, s), 7.20 (1H, t, J=54.1 Hz), 7.37 (1H, d, J=8.6 Hz), 7.47 (1H, s), 7.57 (2H, s), 7.75 (2H, d, J=8.6 Hz), 7.82 (1H, d, J=8.6 Hz), 7.94 (1H, s), 7.95 (2H, d, J=8.6 Hz); mp 235–236° C. (ethanol)

Example 28
7-Fluoro-2-[1-(4-methylsulfonylphenyl)-3-difluoromethyl-1H-pyrazol-5-yl]benzothiazole The procedure of Example 9 was repeated using 1-(7-fluorobenzothiazol-2-yl)-4,4-difluorobutane-1,3-dione and 4-methylsulfonylphenylhydrazine hydrochloride as the starting materials to obtain 7-fluoro-2-[1-(4-methylsulfonylphenyl)-3-difluoromethyl-1H-pyrazol-5-yl]benzothiazole (yield, 63%). NMR(CDCl$_3$) δ: 3.11 (3H, s), 6.81 (1H, t, J=54.8 Hz), 7.09 (1H, app t, J=8.6 Hz), 7.24 (1H, s), 7.48 (1H, dt, J=5.4 Hz, 8.0 Hz), 7.72–7.75 (3H, m), 8.03–8.07 (2H, m); mp 193–195° C. (methanol)

Example 29
4-[5-(7-Fluorobenzothiazol-2-yl)-3-difluoromethyl-1H-pyrazol-1-yl]benzenesulfonamide The procedure of Example 9 was repeated using 1-(7-fluorobenzothiazol-2-yl)-4,4-difluorobutane-1,3-dione and 4-sulfamoylphenylhydrazine hydrochloride as the starting materials to obtain 4-[5-(7-fluorobenzothiazol-2-yl)-3-difluoromethyl-1H-pyrazol-1-yl]benzenesulfonamide (yield, 49%).

NMR(DMSO-$d_6$-D$_2$O) δ: 7.21 (1H, t, J=54.1 Hz), 7.43 (1H, app t, J=8.9 Hz), 7.62 (1H, dt, J=5.6 Hz, 8.1 Hz), 7.62 (1H, s), 7.77–7.80 (2H, m), 7.77–7.84 (1H, m), 7.97–8.01 (2H, m); mp 246–248° C. (toluene)

Example 30
4-[5-(7-Chlorobenzothiazol-2-yl)-3-difluoromethyl-1H-pyrazol-1-yl]benzenesulfonamide The procedure of Example 9 was repeated using 1-(7-chlorobenzothiazol-2-yl)-4,4-difluorobutane-1,3-dione and 4-sulfamoylphenylhydrazine hydrochloride as the starting materials to obtain 4-[5-(7-chlorobenzothiazol-2-yl)-3-difluoromethyl-1H-pyrazol-1-yl]benzenesulfonamide. NMR(DMSO-$d_6$) δ: 7.24 (1H, t, J=54.1 Hz), 7.56–7.68 (5H, m), 7.80 (2H, d, J=8.6 Hz), 7.91–7.97 (3H, m); mp 238–239° C. (ethanol)

Example 31
4-[3-Difluoromethyl-5-(7-methylbenzothiazol-2-yl)-1H-pyrazol-1-yl]benzenesulfonamide The procedure of Example 9 was repeated using 1-(7-methylbenzothiazol-2-yl)-4,4-difluorobutane-1,3-dione and 4-sulfamoylphenylhydrazine hydrochloride as the starting materials to obtain 4-[3-difluoromethyl-5-(7-methylbenzothiazol-2-yl)-1H-pyrazol-1-yl]benzenesulfonamide. NMR(DMSO-$d_6$) δ: 2.54 (3H, s), 7.23 (1H, t, J=54.1 Hz), 7.34–7.57 (5H, m), 7.75–7.78 (3H, m), 7.94 (2H, d, J=8.6 Hz); mp 264–265° C. (ethyl acetate-ethanol)

Example 32
6-Methyl-2-[1-(4-methylsulfonylphenyl)-3-pentafluoroethyl-1H-pyrazol-5-yl]benzothiazole The procedure of Example 9 was repeated using 1-(6-methylbenzothiazol-2-yl)-4,4,5,5,5-pentafluoropentane-1,3-dione and 4-methylsulfonylphenylhydrazine hydrochloride as the starting materials to obtain 6-methyl-2-[1-(4-methylsulfonylphenyl)-3-pentafluoroethyl-1H-pyrazol-5-yl]benzothiazole (yield, 45%).

NMR(CDCl$_3$) δ: 2.45 (3H, s), 3.30 (3H, s), 7.37 (1H, d, J=8.6 Hz), 3 7.80–7.91 (4H, m), 7.98 (1H, s), 8.09 (2H, d, J=8.6 Hz); mp 195–196° C. (ethanol)

Example 33
4-[5-(6-Methylbenzothiazol-2-yl)-3-pentafluoroethyl-1H-pyrazol-5-yl]benzenesulfonamide The procedure of Example 9 was repeated using 1-(6-methylbenzothiazol-2-yl)-4,4,5,5,5-pentafluoropentane-1,3-dione and 4-sulfamoylphenylhydrazine hydrochloride as the starting materials to obtain 4-[5-(6-methylbenzothiazol-2-yl)-3-pentafluoroethyl-1H-pyrazol-5-yl]benzenesulfonamide (yield, 50%).

NMR(CDCl$_3$-DMSO-$d_6$) δ: 2.50 (3H, s), 7.03 (2H, s), 7.34 (1H, d, J=8.2 Hz), 7.53 (1H, s), 7.64 (2H, d, J=8.6 Hz), 7.71 (1H, s), 7.85 (1H, d, J=8.2 Hz), 8.04 (2H, d, J=8.6 Hz); mp 234–235° C. (ethanol)

Example 34

4-[5-(6-Fluorobenzoxazol-2-yl)-3-trifluoromethyl-1H-pyrazol-5-yl]benzenesulfonamide The procedure of Example 9 was repeated using 1-(6-fluorobenzoxazol-2-yl)-4,4,4-trifluorobutane-1,3-dione and 4-sulfamoylphenylhydrazine hydrochloride as the starting materials to obtain 4-[5-(6-fluorobenzoxazol-2-yl)-3-trifluoromethyl-1H-pyrazol-5-yl]benzenesulfonamide. NMR(DMSO-$d_6$) δ6 : 7.35–7.28 (1H, m), 7.59 (2H, bs), 7.78–7.82 (2H, m), 7.90–8.01 (5H, m); mp 297–283° C. (ethyl acetate-diisopropyl ether)

Example 35

4-[5-(6-Methylbenzoxazol-2-yl)-3-trifluoromethyl-1H-pyrazol-5-yl]benzenesulfonamide The procedure of Example 9 was repeated using 1-(6-methylbenzoxazol-2-yl)-4,4,4-trifluorobutane-1,3-dione and 4-sulfamoylphenylhydrazine hydrochloride as the starting materials to obtain 4-[5-(6-methylbenzoxazol-2-yl)-3-trifluoromethyl-1H-pyrazol-5-yl]benzenesulfonamide. NMR(DMSO-$d_6$) δ: 2.46 (3H, s), 7.23–7.27 (1H, m), 7.56–7.64 (4H, m), 7.88–8.02 (5H, m); mp 260–261° C. (methanol-water)

Example 36

6-Fluoro-2-[1-(4-methylsulfonylphenyl)-3-trifluoromethyl-1H-pyrazol-5-yl]benzoxazole The procedure of Example 9 was repeated using 1-(6-fluorobenzoxazol-2-yl)-4,4,4-trifluorobutane-1,3-dione and 4-methylsulfonylphenylhydrazine hydrochloride as the starting materials to obtain 6-fluoro-2-[1-(4-methylsulfonylphenyl)-3-trifluoromethyl-1H-pyrazol-5-yl]benzoxazole.

NMR(CDCl$_3$) δ: 3.14 (3H, s), 7.11–7.18 (1H, m), 7.26–7.30 (1H, m), 7.47 (1H, s), 7.61–7.66 (1H, m), 7.82–7.85 (2H, m), 8.01–8.13 (2H, m); mp 216–218° C. (diisopropyl ether)

Example 37

6-Methyl-2-[1-(4-methylsulfonylphenyl)-3-trifluoromethyl-1H-pyrazol-5-yl]benzoxazole The procedure of Example 9 was repeated using 1-(6-methylbenzoxazol-2-yl)-4,4,4-trifluorobutane-1,3-dione and 4-methylsulfonylphenylhydrazine hydrochloride as the starting materials to obtain 6-methyl-2-[1-(4-methylsulfonylphenyl)-3-trifluoromethyl-1H-pyrazol-5-yl]benzoxazole.

NMR(CDCl$_3$) δ: 2.50 (3H, s), 3.14 (3H, s), 7.19–7.22 (1H, m), 7.33 (1H, s), 7.45 (1H, s), 7.55–7.58 (1H, m), 7.81–7.85 (2H, m), 8.09–8.12 (2H, m); mp 209–210° C. (methanol-water)

Example 38

6-Fluoro-2-[1-(4-methylsulfonylphenyl)-3-trifluoromethyl-1H-pyrazol-5-yl]benzimidazole The procedure of Example 9 was repeated using 1-(6-fluorobenzimidazol-2-yl)-4,4,4-trifluorobutane-1,3-dione and 4-methylsulfonylphenylhydrazine hydrochloride as the starting materials to obtain 6-fluoro-2-[1-(4-methylsulfonylphenyl)-3-trifluoromethyl-1H-pyrazol-5-yl]benzimidazole (yield, 25%).

NMR(DMSO-$d_6$) δ: 3.35 (3, s), 7.12 (1H, bs), 7.40–7.44 (1H, m), 7.58–7.64 (2H, m), 7.83 (2H, d, J=8.3 Hz), 8.06 (2H, d, J=8.5 Hz), 13.3 (1H, bs); mp 278–280° C. (ethyl acetate-isooctane)

Example 39

4-[5-(6-Fluorobenzimidazol-2-yl)-3-trifluoromethyl-1H-pyrazol-5-yl]benzenesulfonamide The procedure of Example 9 was repeated using 1-(6-fluorobenzimidazol-2-yl)-4,4,4-trifluorobutane-1,3-dione and 4-sulfamoylphenylhydrazine hydrochloride as the starting materials to obtain 4-[5-(6-fluorobenzimidazol-2-yl)-3-trifluoromethyl-1H-pyrazol-5-yl]benzenesulfonamide (yield, 24%).

NMR(DMSO-$d_6$) δ: 7.11 (1H, bs), 7.39–7.43 (1H, m), 7.55–7.61 (4H, m), 7.73 (2H, d, J=8.6 Hz), 7.92 (2H, d, J=8.6 Hz), 13.31 (1H, bs); mp 309–310° C. (ethyl acetate-isooctane)

Example 40

4-[5-(4-Methoxybenzothiazol-2-yl)-3-trifluoromethyl-1H-pyrazol-5-yl]benzenesulfonamide The procedure of Example 9 was repeated using 1-(4-methoxybenzothiazol-2-yl)-4,4,4-trifluorobutane-1,3-dione and 4-sulfamoylphenylhydrazine hydrochloride as the starting materials to obtain 4-[5-(4-methoxybenzothiazol-2-yl)-3-trifluoromethyl-1H-pyrazol-5-yl]benzenesulfonamide (yield, 54%).

NMR(DMSO-$d_6$) δ: 3.78 (3H, s), 7.08 (1H, d, J=7.2 Hz), 7.44 (1H, appt, J=8.0 Hz), 7.60 (2H, s), 7.68 (1H, d, J=7.2 Hz), 7.76 (1H, s), 7.81–7.99 (4H, m); mp 276–278° C.

Example 41

4-[5-(4-Fluorobenzothiazol-2-yl)-3-difluoromethyl-1H-pyrazol-5-yl]benzenesulfonamide The procedure of Example 9 was repeated using 1-(4-fluorobenzothiazol-2-yl)-4,4-difluorobutane-1,3-dione and 4-sulfamoylphenylhydrazine hydrochloride as the starting materials to obtain 4-[5-(4-fluorobenzothiazol-2-yl)-3-difluoromethyl-1H-pyrazol-5-yl]benzenesulfonamide (yield, 23%).

NMR(DMSO-$d_6$) δ: 7.24 (1H, t, J=54.1 Hz), 7.38–7.45 (1H, m), 7.49–7.57 (1H, m), 7.59 (2H, brs), 7.59 (1H, s), 7.77–7.83 (2H, m), 8.94–8.03 (3H, m); mp 243–245° C. (ethanol-water)

Reference Example 1

Preparation of 2-acetylbenzazole derivatives (1) 2-Acetyl-6-methylbenzothiazole

A solution of 6-methylbenzothiazole (6.1 g, 41 mmol) in anhydrous THF (150 ml) was cooled to −78° C. To the cooled solution was added, with stirring, n-butyl lithium (28.1 ml of 1.6 M n-BuLi-containing hexane solution, 45 mmol) dropwise under nitrogen atmosphere. Further, a solution of N,N-dimethyl acetamide (3.9 g, 45 mmol) in anhydrous THF (70 ml) was added dropwise to the mixture at the same temperature. After completion of the addition, the mixture was stirred for an hour, and then warmed to room temperature. The reaction mixture was poured into water, and then extracted with benzene. The extract was washed with water, dried over magnesium sulfate, and then evaporated. The resulting residual powders were subjected to purification using column chromatography on silica gel (eluant, n-hexane/ethyl acetate=95/5) to afford 2-acetyl-6-methylbenzothiazole (3.7 g, 47%) as a pale yellow powder, together with the starting material (2.5 g).

NMR(CDCl$_3$) δ: 2.53 (3H, s), 2.81 (3H, s), 7.39 (1H, d, J=1.6 Hz, 8.6 Hz), 7.76 (1H, d, J=1.6 Hz), 8.06 (1H, d, J=8.6 Hz); mp 105–106° C. (n-hexane)

(2) 2-Acetyl-7-fluorobenzothiazole

The procedure of Reference Example 1 (1) was repeated using 7-fluorobenzothiazole as the starting material to obtain 2-acetyl-7-fluorobenzothiazole.

NMR(CDCl$_3$) δ: 2.83 (3H, s), 7.25 (1H, app t, J=8.9 Hz), 7.55 (1H, dt, J=5.3 Hz, 8.2 Hz), 8.00 (1H, dd, J=1.0 Hz, 8.2 Hz)

(3) 2-Acetyl-6-fluoro-5-methylbenzothiazole

The procedure of Reference Example 1 (1) was repeated using 6-fluoro-5-methylbenzothiazole as the starting material to obtain 2-acetyl-6-fluoro-5-methylbenzothiazole (yield, 93%). NMR(CDCl$_3$) δ: 2.44 (3H, q, J=0.6 Hz), 2.79 (3H, s), 7.56 (1H, d, J=8.9 Hz), 7.98 (1H, d, J=7.6 Hz); mp 152–153° C. (ethanol)

For the preparation of Example compounds, other 2-acetyl-benzothiazole derivatives than the aforementioned compounds were prepared according to the above known methods (Bull. Chem. Soc. Jpn., 61, 3637 (1988); J. Chem. Soc., (c), 1971, 1747).

(4) 2-Acetyl-6-fluorobenzoxazole i) To 50 ml of ethanol was added 5-fluoro-2-nitrophenol (7.86 g, 50 mmol) and 10% Pd/C (0.786 g) and the mixture was stirred under a hydrogen stream for 3 hours at room temperature. Then the reaction mixture was filtered and the filtrate concentrated. The residue was subjected to recrystallization from toluene to afford 2-amino-5-fluoro-phenol (5.52 g, yield: 87%).

NMR(DMSO-d$_6$-D$_2$O) δ: 6.38 (1H, dt, J=3.0 Hz, 8.6 Hz), 6.49 (1H, dd, J=3.0 Hz, 10.5 Hz), 6.56 (1H, dd, J=5.3 Hz, 8.6 Hz)

ii) A suspension of 2-amino-5-fluorophenol (5.50 g, 43.3 mmol) and 85–92% lactic acid (6 g) in xylene was refluxed overnight while removing off water by-produced as a result of the reaction. After replacing the solvent with methylene chloride, the resultant mixture was washed with saturated aqueous sodium bicarbonate, water, and saturated aqueous sodium chloride, dried over magnesium sulfate, and then concentrated. The resulting residue was subjected to recrystallization from a mixture of diisopropyl ether and hexane to afford 6-fluoro-2-(1-hydroxyethyl)benzoxazole (4.80 g, yield: 61%).

NMR(CDCl$_3$) δ: 1.71 (3H, d, J=6.6 Hz), 3.03 (1H, bs), 5.10 (1H, q, J=6.6 Hz), 7.09 (1H, dt, J=2.3 Hz, 9.2 Hz), 7.25 (1H, dd, J=2.3 Hz, 7.9 Hz), 7.64 (1H, dd, J=5.0 Hz, 8.9 Hz)

iii) 6-Fluoro-2-(1-hydroxyethyl)benzoxazole (4.71 g, 26 mmol) was dissolved in 100 ml of methylene chloride, and pyridinium chlorochromate (8.38 g, 39 mmol) was added portionwise to the solution. The mixture was stirred for 4 hours at room temperature, then diluted with ether, and filtered. The filtrate was concentrated and the resulting residue was subjected to column chromatography and then recrystallization from methanol to afford 2-acetyl-6-fluorobenzoxazole (1.92 g, yield: 41%).

NMR(CDCl$_3$) δ: 2.80 (3H, s), 7.23 (1H, dt, J=2.6 Hz, 9.2 Hz), 7.37 (1H, dd, J=2.3 Hz, 7.9 Hz), 7.86 (1H, dd, J=4.9 Hz, 8.9 Hz)

(5) 2-Acetyl-6-methylbenzoxazole i) 2-Amino-5-methylphenol as the starting material was reacted with lactic acid in the same manner as in Reference Example 1 (4) ii) to obtain 6-methyl-2-(1-hydroxyethyl)-benzoxazole (yield, 92%).

NMR(CDCl$_3$) δ: 1.70 (3H, d, J=6.9 Hz), 2.49 (3H, s), 5.04–5.14 (1H, m), 7.15 (1H, d, J=8.6 Hz), 7.32 (1H, s), 7.57 (1H, d, J=8.3 Hz)

ii) 6-Methyl-2-(1-hydroxyethyl)benzoxazole as the starting material was reacted with pyridinium chlorochromate in the same manner as in Reference Example 1 (4) iii) to obtain 2-acetyl-6-methylbenzoxazole (yield, 20%).

NMR(CDCl$_3$) δ: 2.54 (3H, s), 2.80 (3H, s), 7.28 (1H, d, J=8.9 Hz), 7.44 (1H, s), 7.76 (1H, d, J=8.3 Hz)

(6) 2-Acetyl-6-fluoroimidazole

A mixture of 4-fluoro-1,2-phenylenediamine (4.38 g, 34.5 mmol), lactic acid (6.2 g, 69 mmol) and 3N hydrochloric acid (3 ml) in xylene was heated under reflux for 48 hours while removing off by-produced water by a Dean-Stark trap. The reaction mixture was evaporated under vacuum. The resulting residue was dissolved in ethyl acetate, and washed with aqueous ammonia, and water. The ethyl acetate layer was dried over magnesium sulfate, and then evaporated. To the residue without purification was added acetic acid (70 ml), water (2 ml) and anhydrous chromic acid (1.3 g, 13 mmol) and the mixture was heated at 65–70° C. for 1.5 hours, and then at 100° C. for one hour. The reaction mixture was evaporated under vacuum and the residue was washed with water. The resulting powders were subjected to column chromatography on silica gel (eluant, ethyl acetate/n-hexane=3/7) to afford 2-acetyl-6-fluoroimidazole (0.8 g, yield: 12.9%). NMR(CDCl$_3$) δ: 2.84 (3H,s), 7.09–7.88 (3H, m), 10.75 (1H,bs); mp 191–193° C. (ethanol)

Reference Example 2

Preparation of 1-benzazol-2-yl-4,4,4-trifluorobutane-1,3-dione derivatives

In a manner similar to the procedure of Example 1.1), using the requisite 2-acetylbenzazole derivatives produced according to the procedure of the above Reference Example 1 or known methods, for reaction with ethyl trifluoroacetate, the following compounds were prepared:

(1) 1-(6-Methylbenzothiazol-2-yl)-4,4,4-trifluorobutane-1,3-dione

NMR(DMSO-d$_6$) δ: 2.49 (3H, s), 6.83 (1H, bs), 7.13 (1H, bs), 7.49 (1H, d, J=1.6 Hz), 8.02 (1H, s), 8.09 (1H, d, J=8.6 Hz)

(2) 1-(7-Fluorobenzothiazol-2-yl)-4,4,4-trifluorobutane-1,3-dione

NMR(CDCl$_3$) δ: 7.18 (1H, bs), 7.26–7.33 (1H, m), 7.59 (1H, dt, J=5.3 Hz, 8.3 Hz), 8.02 (1H, dd, J=1.0 Hz,, 8.3 Hz)

(3) 1-(6-Fluoro-5-methylbenzothiazol-2-yl)-4,4,4-trifluorobutane-1,3-dione NMR(DMSO-d$_6$) δ: 8.16–8.05 (2H, m), 6.75 (1H, brs), 2.50–2.40 (3H, m)

(4) 1-(6-Fluorobenzoxazol-2-yl)-4,4,4-trifluorobutane-1,3-dione (5) 1-(6-Methylbenzoxazol-2-yl)-4,4,4-trifluorobutane-1,3-dione (6) 1-(6-Fluorobenzimidazol-2-yl)-4,4,4-trifluorobutane-1,3-dione (7) 1-(4-Methoxybenzothiazol-2-yl)-4,4,4-trifluorobutane-1,3-dione The above compounds (4) to (7) were used as the starting materials for Examples 34 to 40 without further purification.

Reference Example 3

Preparation of 1-benzazol-2-yl-4,4-difluorobutane-1,3-dione derivatives

In a manner similar to the procedure of Example 1.1), using the requisite 2-acetylbenzazole derivatives produced according to the procedure of the above Reference Example 1 or known methods, for reaction with ethyl difluoroacetate, the following compounds were prepared:

(1) 1-(Benzothiazol-2-yl)-4,4-difluorobutane-1,3-dione (2) 1-(6-Fluorobenzothiazol-2-yl)-4,4-difluorobutane-1,3-dione NMR(CDCl$_3$) δ: 6.12 (1H, t, J=54.1 Hz), 7.09 (1H, s), 7.39–7.32 (1H, m), 7.70–7.66 (1H, m), 8.18–8.13 (1H,m)

(3) 1-(6-Chlorobenzothiazol-2-yl)-4,4-difluorobutane-1,3-dione NMR(CDCl$_3$) δ: 6.12 (1H, t, J=53.8 Hz), 7.10 (1H, bs), 7.57 (1H, dd, J=2.0 Hz, 8.6 Hz), 7.99 (1H, d, J=2.0 Hz), 8.10 (1H, d, J=8.6 Hz)

(4) 1-(6-Methoxybenzothiazol-2-yl)-4,4-difluorobutane-1,3-dione (5) 1-(6-Methylbenzothiazol-2-yl)-4,4-difluorobutane-1,3-dione NMR(CDCl$_3$) δ: 2.54 (3H, s), 6.31 (1H, t, J=53.9 Hz), 7.06 (1H, bs), 7.42 (1H, dd, J=1.5 Hz, 8.3 Hz), 7.79 (1H, d, J=1.5 Hz), 8.06 (1H, d, J=8.3 Hz)

(6) 1-(7-Fluorobenzothiazol-2-yl)-4,4-difluorobutane-1,3-dione NMR(CDCl$_3$) δ: 6.12 (1H, t, J=53.8 Hz), 7.12 (1H, bs), 7.27 (1H, t, J=8.6 Hz), 7.57 (1H, dt, J=5.3 Hz, 8.3 Hz), 8.01 (1H, d, J=8.3 Hz)

(7) 1-(7-Chlorobenzothiazol-2-yl)-4,4-difluorobutane-1,3-dione (8) 1-(7-Methylbenzothiazol-2-yl)-4,4-difluorobutane-1,3-dione (9) 1-(4-Fluorobenzothiazol-2-yl)-4,4-difluorobutane-1,3-dione The above compounds (1), (4), (7), (8) and (9) were used as the starting materials for Examples 21, 25, 30, 31 and 41 without further purification.

Reference Example 4

Preparation of 1-benzazol-2-yl-4,4,5,5,5-pentafluoropentane-1,3-dione derivatives In a manner similar to the procedure of Example 1.1), using the requisite 2-acetyl-6-methylbenzothiazole and ethyl pentafluoropropionate, the following compounds were prepared:

1-(6-Methylbenzothiazol-2-yl)-4,4,5,5,5-pentafluoropentane-1,3-dione

NMR(DMSO-d$_6$) δ: 2.50 (3H, s), 6.81 (1H, bs), 7.07 (1H, bs), 7.47 (1H, dd, J=1.3, 8.2 Hz), 8.02 (1H, d, J=1.3 Hz), 8.10 (1H, d, J=8.2 Hz)

Formulation Examples

Formulation Example 1

A formula for one tablet (total amount per tablet: 180 mg) is given below:

| Compound of the present invention | 50 mg |
| --- | --- |
| Crystalline Cellulose | 100 mg |
| Maize Starch | 28 mg |
| Magnesium Stearate | 2 mg |

The ingredients were formulated into tablets by known methods according to general pharmaceutical rules prescribed in JPXIII.

Formulation Example 2

A formula for one capsule (total amount per capsule: 180 mg) is given below:

| Compound of the present invention | 50 mg |
| --- | --- |
| Lactose | 100 mg |
| Maize Starch | 28 mg |
| Magnesium Stearate | 2 mg |

The ingredients were formulated into capsules by known methods according to general pharmaceutical rules prescribed in JPXIII.

Formulation Example 3

The compound of the present invention (100 mg) was dissolved in 15 ml of aqueous physiological saline. The solution was adjusted to pH 7 with 0.1 N aqueous sodium hydroxide, to which was added an aqueous physiological saline to make the total volume 20 ml. The resulting solution was dispensed to each ampoule, and then subjected to heat sterilization to obtain injections.

Formulation Example 4

The pulverized compound of the present invention (100 mg) was mixed with 10 g of Witepsol (H-15) (Dynamit Nobel) heat-melted to 70° C. and dispersed therein. The dispersion was poured into a suppository mold, and allowed to cool and solidify. The finished suppositories were removed from the mold.

Formulation Example 5

The pulverized compound of the present invention (100 mg) was well mixed with white petrolatum to form an ointment.

Industrial Applicability

The present invention relates to novel pyrazole derivatives having a benzazole moiety and to pharmaceutical drugs for controlling or alleviating inflammation and various symptoms associated therewith, such as pain. The compounds of the present invention have potent inhibitory actions on COX-2 induced in inflamed sites upon inflammation while relatively weak inhibitory ones on COX-1 present in stomach, kidney, and the like, thereby enabling us to selectively inhibit the biosynthesis of prostaglandins in the inflamed sites. The compounds are useful as selective COX-2 inhibitors and anti-inflammatory drugs rarely accompanying adverse actions including attacks on gastric mucosa and/or kidney.

What is claimed is:

1. A compound of the formula (1):

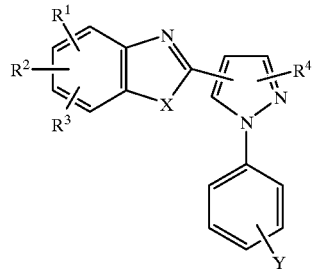

(1)

wherein $R^1$ is hydrogen or halogen, $R^2$ and $R^3$ are each independently hydrogen, halogen, lower alkyl, lower alkoxy, hydroxy or lower alkanoyloxy, $R^4$ is lower haloalkyl or lower alkyl, X is sulfur, oxygen or NH, and Y is lower alkylthio, lower alkylsulfonyl or sulfamoyl, or a pharmaceutically acceptable salt thereof.

2. A compound of the formula (2):

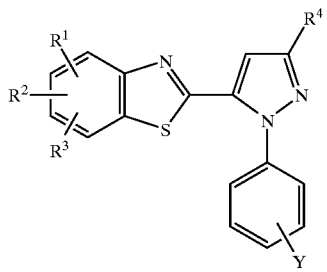

(2)

wherein $R^1$ is hydrogen or halogen, $R^2$ and $R^3$ are each independently hydrogen, halogen, lower alkyl, lower alkoxy, hydroxy or lower alkanoyloxy, $R^4$ is lower haloalkyl or lower alkyl, and Y is lower alkylthio, lower alkylsulfonyl or sulfamoyl,
or a pharmaceutically acceptable salt thereof.

3. The compound according to claim 2, wherein $R^4$ is lower haloalkyl, and Y is lower alkylsulfonyl, or sulfamoyl, or a pharmaceutically acceptable salt thereof.

4. A pharmaceutical composition which comprises an effective amount of a compound according to claim 1 or a pharmaceutically acceptable salt thereof in admixture with a pharmaceutically acceptable carrier.

5. A method for inhibiting COX-2 in a patient in need thereof, which comprises administering to the patient a therapeutically effective amount of the compound according to claim 1 or a pharmaceutically acceptable salt thereof.

6. A method for treating inflammation in a patient in need thereof, which comprises administering to the patient a therapeutically effective amount of the compound according to claim 1 or a pharmaceutically acceptable salt thereof.

* * * * *